United States Patent [19]
Rajala et al.

[11] Patent Number: 6,098,203
[45] Date of Patent: Aug. 8, 2000

[54] DISPOSABLE GARMENT AND RELATED MANUFACTURING EQUIPMENT AND METHODS

[75] Inventors: Gregory John Rajala, Neenah; Steven Craig Gehling, Oshkosh; Paul Daniel Suke, Appleton, all of Wis.

[73] Assignee: Kimberly-Clark Worldwide, Inc., Neenah, Wis.

[21] Appl. No.: 08/959,622

[22] Filed: Oct. 28, 1997

Related U.S. Application Data

[63] Continuation of application No. 08/382,108, Jan. 31, 1995, Pat. No. 5,745,922.

[51] Int. Cl.$^7$ ...................................................... A41B 9/00
[52] U.S. Cl. .................................. 2/401; 2/111; 2/243.1; 2/403; 2/406; 604/385.2; 604/396
[58] Field of Search ............................. 2/111, 400, 401, 2/402, 406, 403; 604/358, 385.1, 385.2, 394, 396

[56] References Cited

U.S. PATENT DOCUMENTS

| | | | |
|---|---|---|---|
| 2,581,904 | 1/1952 | Burns ........................................... | 2/111 |
| 3,488,778 | 1/1970 | Goujon et al. ............................... | 2/111 |
| 3,560,292 | 2/1971 | Butter ........................................... | 2/111 |
| 3,599,640 | 8/1971 | Larson ..................................... | 128/286 |
| 4,205,679 | 6/1980 | Repke et al. .............................. | 128/287 |
| 4,610,680 | 9/1986 | Lafleur ...................................... | 604/385 |
| 4,619,649 | 10/1986 | Roberts .................................... | 604/396 |
| 4,743,241 | 5/1988 | Igaue et al. .............................. | 604/385 |
| 4,960,414 | 10/1990 | Meyer ....................................... | 604/395 |
| 5,080,741 | 1/1992 | Nomura et al. .......................... | 156/201 |
| 5,163,932 | 11/1992 | Nomura et al. ....................... | 604/385.2 |

*Primary Examiner*—John J. Calvert
*Assistant Examiner*—Katherine Moran
*Attorney, Agent, or Firm*—Michael L. Winkelman

[57] ABSTRACT

This invention pertains to a three dimensional disposable garment, subassemblies of the garment, and apparatus and methods for making the garment and subassemblies. The garment is designed to hold a primary absorbent sanitary pad. The garment may have elasticized leg and waist openings and be stretchable about the hip and stomach regions of a user. The garment provides backup protection to control egress of fluids that leak or seep around or through the primary sanitary pad. The garment includes a secondary absorbent positioned in the crotch area and extending into the body of the disposable garment, front and back, and preferably over the leg elastics to trap, inside the garment, leakage from the primary absorbent, and to prevent strike through onto e.g. outer clothing and bed linen. The apparatus and methods facilitate assembling leg elastics and crotch elastics into the garment subassemblies while assembling a series of garment subassemblies in a continuous web structure at a constant, or relatively constant, continuous and efficient speed.

24 Claims, 13 Drawing Sheets

DISPOSABLE GARMENT AND RELATED MANUFACTURING EQUIPMENT AND METHODS

CROSS REFERENCE TO RELATED APPLICATIONS

This application is a continuation of application Ser. No. 08/382,108 filed Jan. 31, 1995, which issued May 5, 1998 as U.S. Pat. No. 5,745,922.

FIELD OF THE INVENTION

This invention relates to undergarments in general, and more specifically to women's disposable undergarments having an absorbent layer or fluid repellent region or both to be used with a woman's normal feminine care protection during her menstrual period.

BACKGROUND OF THE INVENTION

Regular undergarments in current use are made of cotton and/or synthetic materials. The cotton and synthetic panties typically do not offer barrier protection. Often the synthetic panties have a cotton lined crotch to absorb vaginal discharges or perspiration. The absorbent/barrier properties of regular undergarments are minimal such that any vaginal discharge and/or heavy perspiration may strike through onto outer clothing (i.e. liquid penetrates from the interior to the exterior of the undergarment.)

Panty liners and feminine care sanitary napkins or pads used with regular undergarments have polyethylene backings that provide some barrier properties inhibiting liquid strike through. However, if the vaginal discharge extends to the sides or the ends of the pads it can leak or seep around an edge of the pad and onto the undergarment. Such leakage can stain the undergarment. Depending upon the amount of leakage, liquid may strike through or go around the undergarment and stain outer clothing and/or bedding. Women with heavy liquid flows may use one or more maxi pads, double pads and/or tampons alone, or in combination, and change these pads and tampons frequently to prevent embarrassing, messy leakage around the edges of the pads and/or staining of outer clothing. In some cases, during their heaviest flow days, some women will restrict their activities and stay home.

Many women experience some leakage of menses from their pads to their undergarments. This varies from being limited to a small number of pads leaking onto only the undergarment during light flow to more prevalent leakage onto the wearer's outer clothing on pads worn during heavy flow. Normally this leakage occurs at the side of the pad, although end leakage is also a problem. Placement of maxi pads and overnight pads in the crotch of regular undergarments shows that, at best, the pads lay on the leg elastic and, at worst, overhang the leg elastics. This causes side leakage onto the undergarment and possibly onto outer clothing. Typical leakage from the pad is caused by poor fit of the pad to the body, improper positioning of the pad by the user and lack of absorbency. Leakage from the undergarment onto the outer clothing is typically due to incompatibility between the pad width and the undergarment crotch width and/or lack of barrier properties in the undergarment material around the edge portion of the pad.

SUMMARY OF THE INVENTION

This invention describes a three dimensional, disposable, discrete garment, subassemblies of the garment, and apparatus and methods for making the garment.

First the invention describes a garment blank subassembly which is a type of precursor of the garment. The subassembly has a front body portion, a back body portion, and an intermediate crotch extending from the front body portion to the back body portion and between a pair of leg cutouts for defining leg openings in the garment to be assembled from the garment blank subassembly. The front body portion has first and second front leg edge portions along the leg cutouts. The back body portion has third and fourth back leg edge portions along the leg cutouts. Fifth and sixth crotch edge portions are disposed on opposing sides of the crotch along the leg cutouts. The front body portion has a front waist portion at a first edge of the garment blank subassembly. The back body portion has a back waist portion at a second edge of the garment blank subassembly opposite the first edge, the front and back body portions, in combination, defining opposing third and fourth side edges of the garment blank subassembly. The garment blank subassembly has a length extending between the first and second edges, and a width extending between the third and fourth edges. Each of the third and fourth back leg edge portions has a first angular portion extending generally along a line forming an acute angle with an imaginary centerline extending between the first and second edges, and a second arcuate portion having a third end at the respective first angular portion and a fourth end connecting the respective back leg edge portion to the respective one of the fifth and sixth crotch edge portions. The garment blank subassembly, when laid out flat, comprises a first operative layer, generally extending functionally from the first edge through the crotch to the second edge; a second layer secured to the first layer; and one or more threads of elastic between and secured to the first and second layers, and extending continuously from a first locus adjacent the third side edge, as a first section, along the width of the garment blank subassembly, toward the first edge at an acute angle with the centerline and generally following the third back leg edge portion toward the crotch, as a second section across the crotch, and as a third section along the width of the garment blank subassembly and away from the first edge at an acute angle with the centerline and generally following the fourth back leg edge portion, to a second locus adjacent the fourth side edge.

Preferably, the first and third sections of elastic are stretched when the garment blank subassembly is laid out flat, and the second section of elastic is substantially relaxed.

In preferred embodiments, the elastic extends across the crotch between the two fourth ends of the second arcuate portions and parallel to the second edge of the garment blank subassembly.

In some embodiments, it is preferred that the second section of elastic be disposed and secured between the first and second layers.

Typically, the second layer comprises a body side liner having a front layer element secured to the front portion of the first layer, and a back layer element secured to the back portion of the first layer, with an unsecured space disposed between the front layer element and the back layer element, the unsecured space generally corresponding with the crotch portion of the garment blank subassembly, the second section of elastic preferably being disposed in the unsecured space, between the front and back layer elements of the first layer.

The term "unsecured space" may include an area where the front layer element and the back layer element of the second layer may or may not be contiguous and which at least a portion of the front and/or back layer elements remain unsecured to the first layer or an area on the first layer between the front layer element and the back layer element which lacks a second layer. The unsecured areas do not include those zones typically formed between swirls or lines of adhesive but rather block zones lacking adhesive or other bonding applications.

Further to preferred embodiments, each of the first and second front leg edge portions has a first longitudinal portion extending generally along the width of the garment blank subassembly and a second arcuate portion having a first end at the respective first longitudinal portion and a second end connecting the respective front leg edge portion to the respective one of the fifth and sixth crotch edge portions, the garment blank subassembly including a separate thread of elastic between and secured to the first and second layers and extending from a third locus adjacent the third side edge, as a fourth section of elastic, along the width of the garment blank. subassembly, generally following the first front leg edge portion along the first longitudinal portion and along at least part of the respective first arcuate portion, away from the first edge, to the crotch, as a fifth section across the crotch, and as a sixth section along at least part of the respective second arcuate portion of the respective front leg edge portion, toward the first edge and generally following the second front leg edge portion along the second longitudinal portion to a fourth locus adjacent the fourth side edge.

Preferably, a second and optionally additional threads of elastic follow a path generally parallel to the path followed by the first thread of elastic. Additional threads of elastic may be disposed along the fifth and sixth crotch edge portions.

Second, the invention comprehends a garment blank subassembly wherein each of the first and second front leg edge portions has a longitudinal portion extending generally along the width of the garment blank subassembly and a first arcuate portion having a first end at the respective first longitudinal portion and a second end connecting the respective front leg edge portion to the respective one of the fifth and sixth crotch edge portions, and wherein one or more threads of elastic are disposed between and secured to the first and second layers, and extend continuously from a first locus adjacent the third side edge, as a first section, along the width of the garment blank subassembly, generally following the first front leg edge portion along its first longitudinal portion and along at least part of the respective first arcuate portion, away from the first edge, toward the crotch, as a second section across the crotch, and as a third section along at least part of the respective first arcuate portion, toward the first edge and generally following the second front leg edge portion along the second longitudinal portion to a locus adjacent the fourth side edge. The elastic generally extends across the crotch between the second ends of the first arcuate portions and the first edge of the garment blank subassembly. The first and third sections of elastic are typically stretched when the garment blank subassembly is laid out flat, the second section of elastic being relaxed.

In some embodiments, the second section of threads of elastic, which has been described as extending across the crotch, at either or both of the. front and back leg edge portions, is cut or portions of the threads are cut such that the second section, or portions of it, extend from one or both of the respective first and third sections, generally at the crotch. In such instance, the length of the second section, in its essentially relaxed state, may be shorter than the distance separating the first and third sections.

Third, the invention comprehends a disposable garment adapted to receive a primary absorbent, the primary absorbent having a liquid permeable inner sheet to be disposed against the user's body, a liquid impermeable outer sheet, and an absorbent member disposed therebetween. The disposable garment comprises an outer cover having front and back body portions connected by a crotch portion, the crotch portion, when laid out flat, having a length, and at any given point along the length, and a width, the front and back body portions being connected together to form a waist opening and first and second leg openings; and an absorbent composite associated with the crotch portion. The outer cover of the garment comprises a first outer layer. A second inner layer is in contact with the first outer layer. One or more continuous threads of elastic is disposed between, and secured to, the first and second layers. First and second sections of the elastic extend along the first and second leg openings, thereby to form puckers about the first and second leg openings at edges thereof. A third section of the elastic extends across the crotch in an essentially relaxed state, such that the width of the crotch portion in the assembly corresponds generally to the width of the crotch portion when the crotch portion is laid out flat.

Preferably, the second inner layer has first and second sides, the elastic is disposed on the first side of the second inner layer, and the absorbent composite is disposed on the second side of the second inner layer.

Also preferably, the first and second sections of the elastic are separated from the absorbent composite by the second inner layer, with the third section of elastic being disposed between the first and second layers.

In some embodiments, the second layer comprises a body side liner having a front layer element secured to the front portion of the first layer, and a back layer element secured to the back portion of the first layer, and including an unsecured space between the front layer element and the back layer element, with the third section of elastic disposed in the unsecured space between the front and back portions of the first layer.

Preferably, the elastic defines a first path of traverse across the garment, and the garment includes at least a second thread of elastic following a second path generally parallel to the first path.

Preferably, the combination of the elastics circumscribe substantial portions of, and potentially encircle the first and second leg openings, at the corresponding edges of the leg openings, thereby providing substantially continuous expansible puckering about the leg openings.

Fourth, the invention comprehends apparatus for placing and securing one or more threads of elastic between first and second layers of a continuous web in producing a series of garment or other garment subassemblies longitudinally along the web, the subassemblies to be separated from the web. Regarding garments, each garment has a front portion, a back portion, a crotch portion connecting the front and the back portions, a waist opening and leg openings, the length of a given garment subassembly, front-to-back, in the continuous web being disposed transverse to the longitudinal direction of advance of the garment subassemblies through the apparatus. Given the foregoing product descriptions, the apparatus comprises first and second rolls comprising a nip, for joining elements of the garment subassemblies; first means such as unwind, drive, and guide apparatus, for feeding first and second webs comprising corresponding first and second layers of the garment subassembly into the nip; an adhesive applicator for placing adhesive on the second web; a supply of elastic, for example including unwind and drive apparatus, for supplying one or more threads of elastic for use at the nip and in contact with the adhesive; a lateral guide, disposed in a lateral position with respect to the second web within one inch of the nip and adjacent the second web, for receiving the elastic, for feeding the elastic to the nip between the first and second webs, and for controlling the lateral position of the elastic as the elastic enters the nip; and a transverse driver for maintaining the lateral guide within the one inch of the nip and for driving the lateral guide in a transverse direction across the width of the second web and thereby changing the lateral position of the lateral guide with respect to the web adjacent the nip, and thus causing the elastic to follow a path on the second web corresponding to edges of the leg openings, in registration with advance of the respective ones of the series of garment subassemblies.

Preferably, the lateral guide is disposed within 0.5 inch of the nip, and is positioned to direct the elastic onto the adhesive on the second web before the elastic enters the nip.

The apparatus preferably includes a cutter for cutting the leg openings, and thereby creating the edges of the leg openings which correspond in registration with the lateral positions of the elastic, such that the elastic follows a path on the subassembly parallel to the leg openings across the transverse dimension of the garment subassembly to a locus at least adjacent the:crotch.

Fifth, the invention comprehends a method of placing and securing an elastic thread between first and second layers of a continuous web in producing a series of garment-type assemblies or subassemblies, each garment-type assembly or subassembly having at least one opening. The method comprises the steps of feeding first and second webs comprising corresponding first and second layers of the garment-type assembly into a nip; applying adhesive on the second web ahead of the nip; supplying one or more threads of elastic for use at the nip and in contact with the adhesive; feeding the elastic to a lateral guide, disposed in a lateral position with respect to the second web within one inch of the nip and adjacent the second web, and thus receiving the elastic, and feeding the elastic to the nip between the first and second webs, and controlling the lateral position of the elastic as the thread enters the nip; and maintaining the lateral guide within two inch of the nip, and driving the lateral guide in a transverse direction across the width of the second web and thereby changing the lateral position of the lateral guide with respect to the web adjacent the nip, and thus causing the elastic to follow a path corresponding to an edge of the opening, in registration with advance of the respective ones of the series of garmenttype assemblies or subassemblies.

The method preferably includes disposing the lateral guide within 0.5 inch of the nip, preferably directing the elastic onto the adhesive on the second web before the elastic enters the nip, and cutting the opening, and thereby creating the edge of the opening which corresponds in registration with the lateral positions of the elastic, such that once the opening is cut, the previously-incorporated elastic follows a path generally parallel to the opening across the transverse dimension of the garment-type assembly or subassembly.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE ILLUSTRATED EMBODIMENTS

The following detailed description is made in the context of an article including a disposable garment, and corresponding garment subassemblies, for holding a sanitary pad in place as a primary absorbent during use of the garment. It is readily apparent, however, that the garments made using the present invention can be employed with other disposable sanitary articles, such as feminine tampons, incontinent garments, diapers, training pants, and the like.

Figure 1:
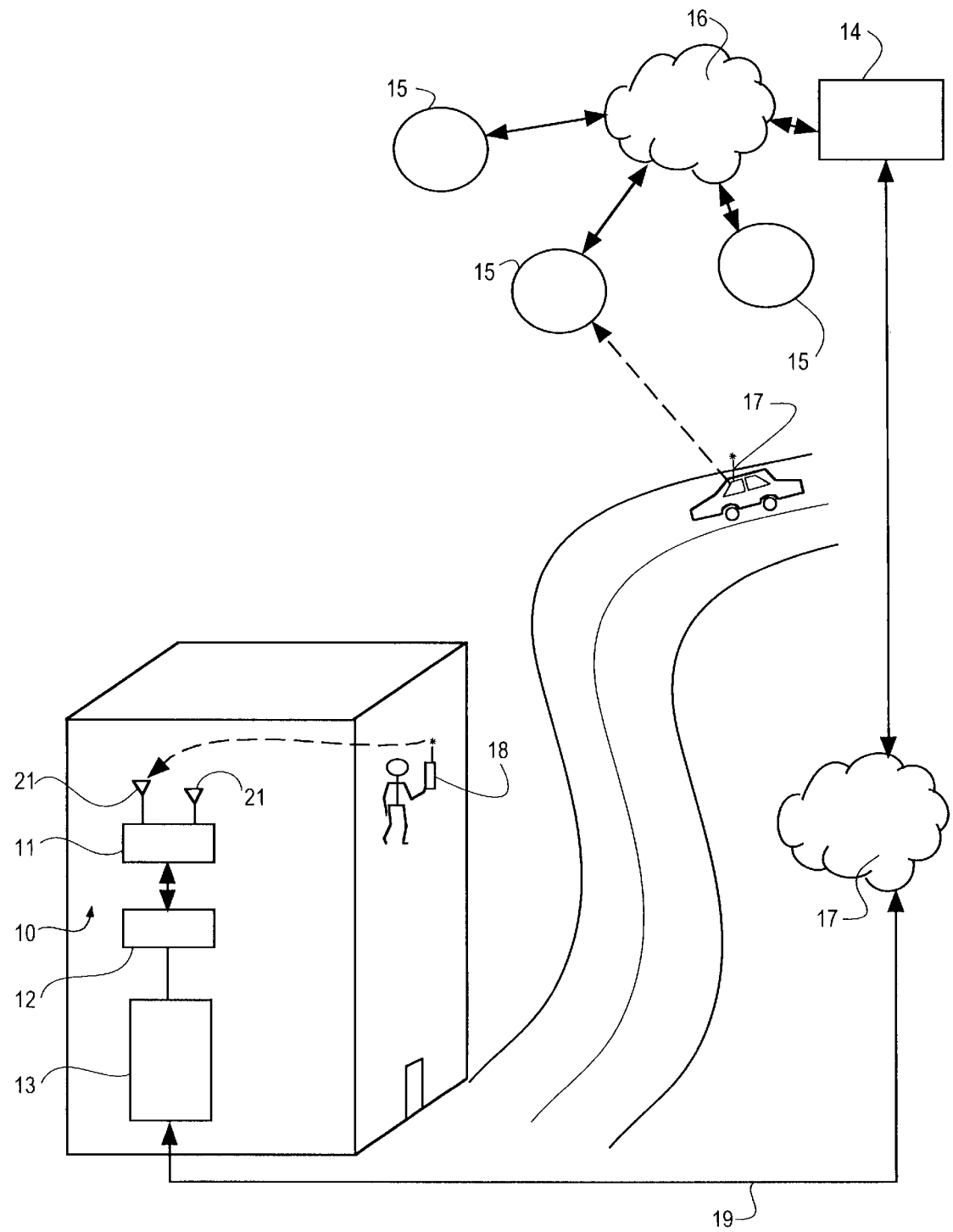
FIG. 1 is a plan view of a garment subassembly relating to an garment of the invention.
Figure 2:
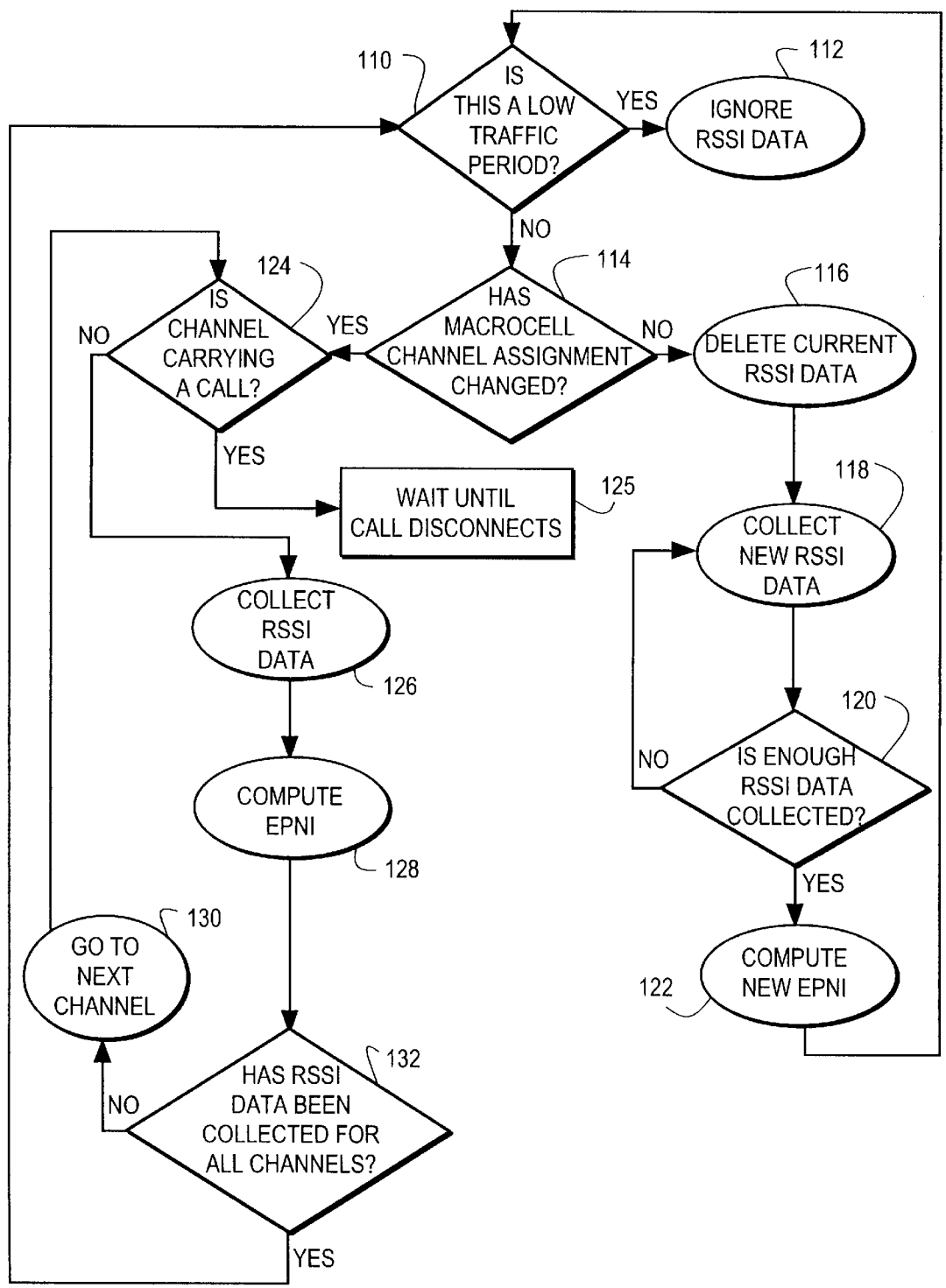
FIG. 2 is a plan view of the garment subassembly of FIG. 1, including the secondary absorbent in the crotch.
Figure 3:
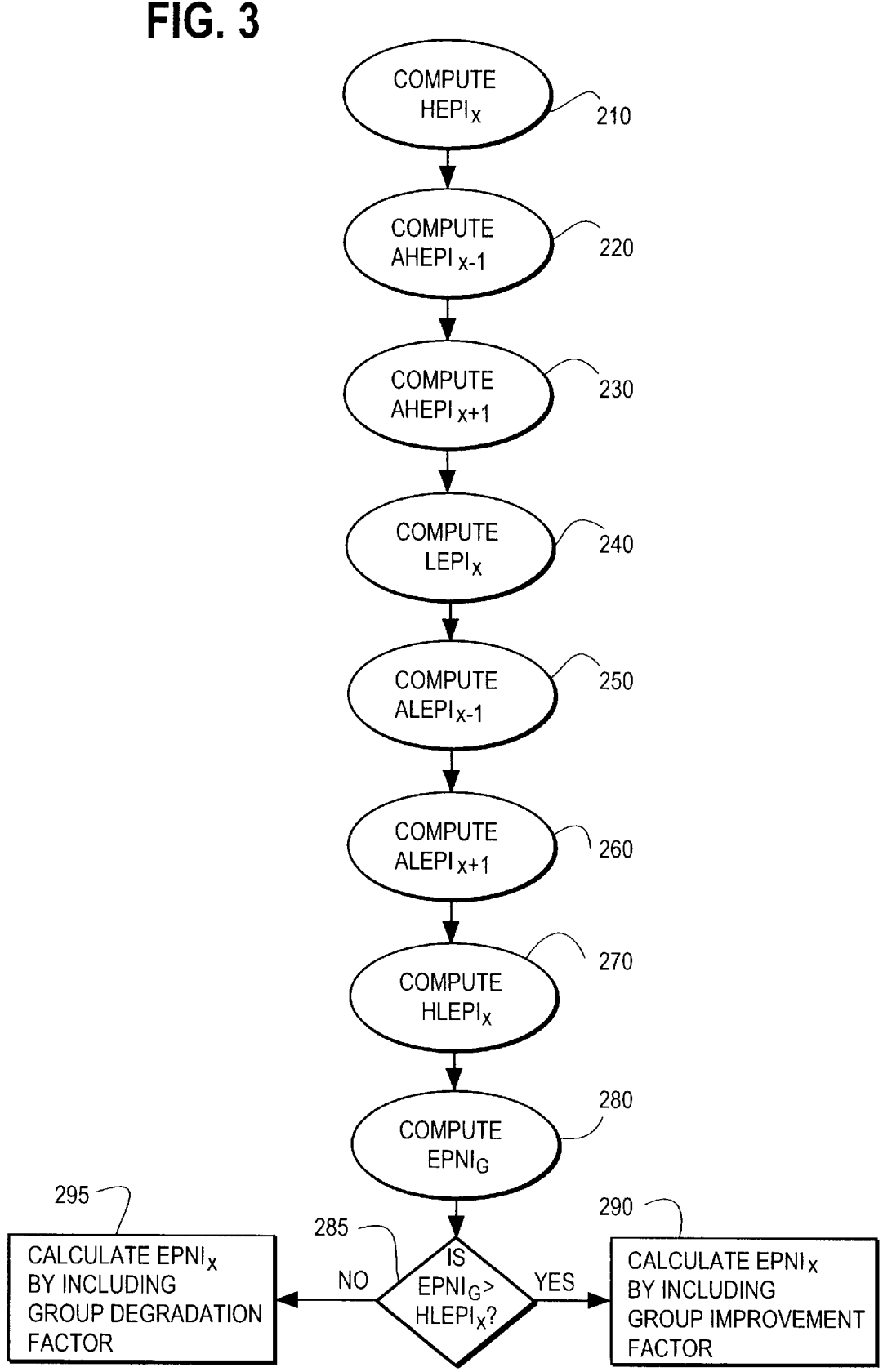
FIG. 3 is a cross section of the garment subassembly taken at 3—3 of FIG. 2.
Figure 5:
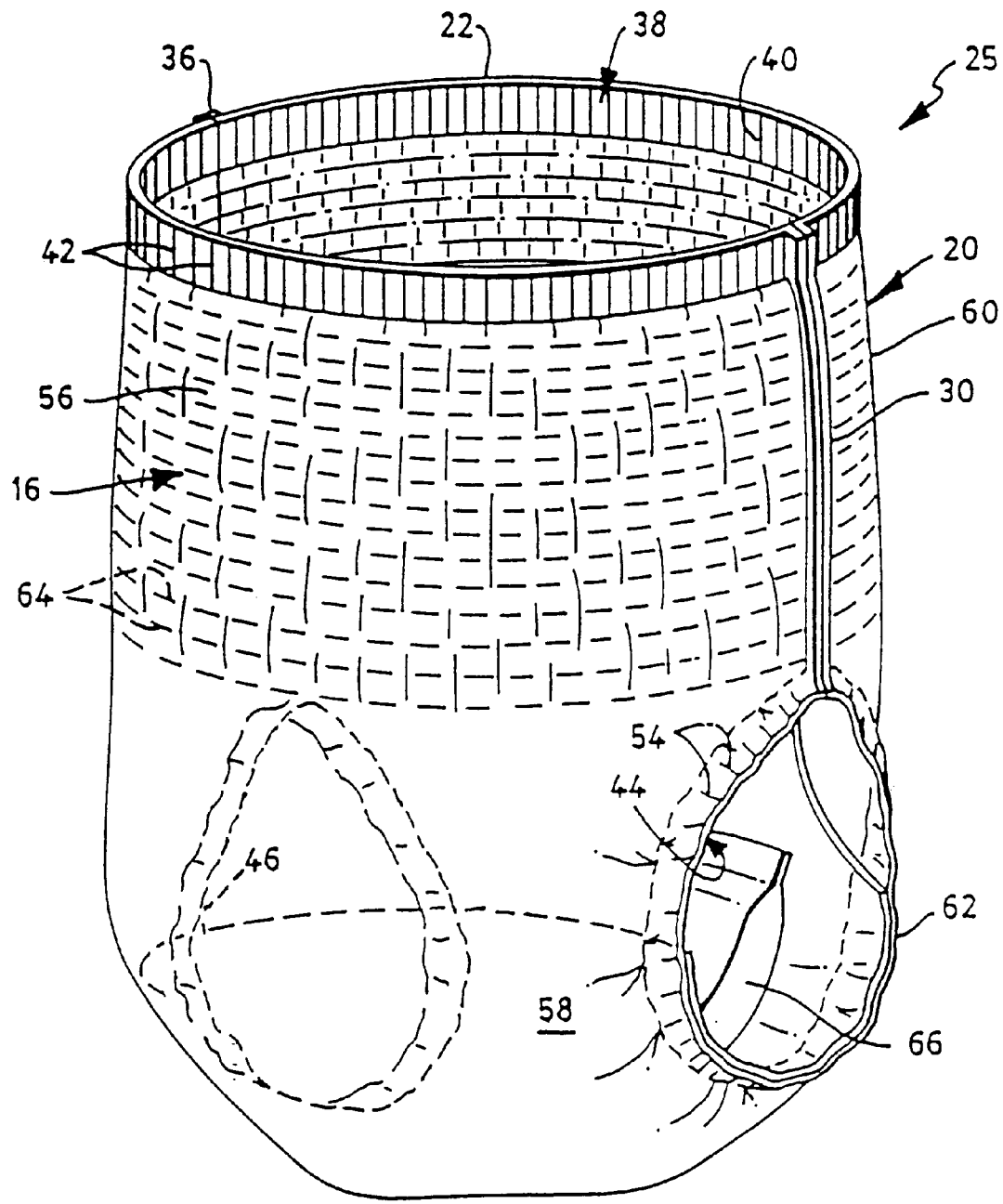
FIG. 5 is a perspective view of a disposable garment of the invention.

The garment subassembly 10 of FIG. 1 illustrates the preferred embodiment of the two-layer garment subassembly prior to incorporation of the secondary absorbent. The garment subassembly of FIG. 2 illustrates the preferred embodiment of the finished garment including all elements, but before the final steps of assembling the composite to form the garment structure. FIG. 5 shows the finally-assembled disposable garment structure. Referring to FIGS. 1–3, the garment subassembly 10 has an outer cover layer 12 generally defining the overall length "L1" and width "W1" of the subassembly, and at least one body side layer(s) 14 secured to the outer cover layer to cover adhesively applied components. The garment subassembly 10 generally includes a front body portion 16 terminating at a front waist portion 18 as a first edge of the subassembly, a back body portion 20 terminating at a back waist portion 22 as a second edge of the subassembly, and a crotch portion 24.

Advantageously, the body side layer 14 includes a front layer element 19 generally overlying and secured to the outer cover layer 12 on the front body portion 16, and a back layer element 21 generally overlying,and secured to the outer cover layer 12 on the back body portion 20. A unsecured space 23 separates the front layer element 19 from the back layer element 21.

Referring to FIGS. 2 and 5, for assembling the subassembly of FIG. 2 to form an garment 25 as in FIG. 5, a first side edge 26 of front body portion 16 is assembled with a first side edge 28 of the back body portion 20 to form a first side seal 30. Similarly, a second side edge 32 of the front body portion 16 is assembled with a second side edge 34 of the back body portion 20 to form a second side seal 36. The waist portions 18, 22 when assembled form a waist opening 38 for putting on and taking off the garment 25. The waist opening 38 is surrounded at least in part by a waist elastic 40. The waist elastic 40 is stretched and attached to the waist portions 18, 22 in the stretched state. The waist elastic 40 is released after attachment to produce waist folds or pleats 42 to allow expansion of the waist opening 38 so that the garment 25 can fit various sizes of people. Because users of this invention generally prefer a brief style garment, the front waist portion 18 preferably comes as high as the navel and is level around the wearer's waist. Having the garment at this height provides a snug fit. Alternative garment styles include bikini (e. g. regular leg cut or french leg cut) and hipster (e.g. regular leg cut or french leg cut).

Referring to FIGS. 1 and 5, the front body portion 16, the back body portion 20, and the crotch portion 24, in combination, form left and right leg openings 44 and 46, respectively, which are generally circular or oval in shape in the finally assembled garment 25. The leg openings 44 and 46 are formed by cutting away portions of the outer cover layer 12, and corresponding portions if any of body side layer 14. Each leg opening 44, 46 is surrounded at least in part by a back leg elastic 48, a front leg elastic 50, and a crotch elastic 51 between the back leg elastic and the front leg elastic. Each of the respective elastics 48, 50, 51 is adjacent the respective one of the edges 52 of the corresponding leg openings. The front and back leg elastics 48, 50 are secured between the outer cover layer 12 and the body side layer 14 by adhesive 55. The crotch elastics 51 are secured to outer cover layer 12 by adhesive 55. The elastics 48, 50, 51 are in the stretched state when secured to the outer cover layer 12. Accordingly, when the elastics, the outer cover layer and the body side layer are released after the elastics are secured to the outer cover layer, the elastics produce leg folds or pleats 54 at the edges of the leg openings 44, 46 to allow expansion of the leg openings 44, 46 to fit various sizes of legs. Between the front body portion and the back body portion in generally the crotch portion of the garment, an unsecure area is created. The unsecured area can be substantially unsecured or relatively unsecured in comparison to the attachment of the front and back portions to the first layer.

The front body portion 16 may be divided into a front upper portion 56 and a front lower portion 58. Similarly, the back body portion 20 may be divided into a back upper portion 60 and a back lower portion 62. The upper portions 56 and 60 are preferably designed to include body elastics 64 which readily stretch to allow the wearer to put on the garment 25 and then readily contract to resume the normal release state of the body elastics. This ensures a close or snug fit to different body sizes and forms. A number of body elastics 64 are positioned on both the front and the back portions 56, 60, respectively, at positions between the waist opening 38 and the leg openings 44, 46, so that the garment 25 has a good fit, particularly around the body.

The lower body portions 58, 62 generally do not require the spaced elastics as in the upper body portions 56, 60, although the elastics may be used.

The width of the crotch portion 24 between the left and right crotch elastics 51 should be wide enough to accommodate laying the primary absorbent 66 between the edges 52 without having the primary absorbent 66 obstruct the crotch elastics 51. This allows the crotch elastics 51 to contract and draw up the sides of the crotch about the primary absorbent, to thus accommodate the thickness of the primary absorbent 66, and to give surface area within the crotch portion 24 of the garment, adjacent edges 52, to contain leakage from the primary absorbent 66.

The width of the crotch portion 24 between the elastics 51 should not be so wide as to seem bulky or uncomfortable. A suitable width is at least about 2.75 inches (70 mm) between the crotch elastics. Width of crotch portion 24 is advantageous from about 3 inches (76 mm) to about 3.5 inches (89 mm). Preferably, the width is about 3 inches (76 mm).

Preferably, the crotch elastics 51 are from about 0.375 inch (10 mm) to about 0.625 inch (16 mm) wide. More preferably, the width is about 0.5 inch (13 mm). Preferably, ruffle material on the edge of the leg openings 44, 46 outside the leg elastics 48, 50 and crotch elastics 51 is less than about 0.25 (6 mm). More preferably, the ruffle material is less than about 0.125 inch (3 mm). It is most desirable to eliminate any ruffle material from the edges of the leg openings 44, 46, as illustrated in FIG. 5.

The overall width of the crotch portion 24 includes the width between the left and right crotch elastics 51, the width of the crotch elastics, and any ruffle material outside the crotch elastics to the edges 52 of the leg openings. Preferably, the overall width of the crotch portion 24 should be at least about 4 inches (102 mm).

FIG. 2 shows the garment subassembly 10 of FIG. 1 with a secondary absorbent 68 secured in the crotch portion 24, over the outer cover layer 12 and parts of the front and back layer elements 19, 21 of the body side layer 14. The width of the secondary absorbent 68 is sized in relation to the width of the crotch portion 24. Preferably, the width of the secondary absorbent 68 is at least the width of the crotch portion 24 between the crotch elastics 51. More preferably, the width of the secondary absorbent is equivalent to the overall width of the crotch portion 24.

The secondary absorbent 68 should have sufficient capacity to absorb any flow or seepage of body fluid around or through the primary absorbent 66. The secondary absorbent 68 should preferably have a capacity and thickness substantially less than that of the primary absorbent 66, thus providing a nonbulky and flexible fit. The secondary absorbent 68 should have a total capacity of about one-half the capacity of the primary absorbent 66. Preferably, the secondary absorbent 68 should have a total capacity of at least about 3 grams and not more than 6 grams. More preferably, the total capacity of the secondary absorbent 68 should be from about 4 grams to about 6 grams. However, the basis weight of, or the type of, the secondary absorbent 68 should be selected to provide resistance to flexibility of less than around 400 grams, as measured by INDA Standard Test method IST 90.3-92 Standard Test Method for Handle-O-Meter Stiffness of Nonwoven Fabrics.

The secondary absorbent has a low stiffness. The low stiffness allows the absorbent and its barrier to remain attached to the conformable outer cover layer 12 and the body side layer 14 which conform to a wide range of body sizes and shapes. Preferably, the secondary absorbent has a stiffness of less than 400 grams along any axis tested, more preferably less than 300 grams along any axis and less than 100 grams along the axis parallel to the waist opening. The secondary absorbent alone will have a stiffness of less than 250 grams and preferably less than 100 grams along any axis and more preferably less than 75 grams along the axis parallel to the waist opening.

The overall length of the secondary absorbent 68 should be adequate to extend beyond the ends of the primary absorbent 66, in order to be properly positioned to receive liquid which flows or seeps around the edges of the primary absorbent 66. This overall length is typically at least about 15 inches (382 mm) thus extending beyond the crotch portion 24 along the longitudinal centerline A—A of the subassembly 10. The length should be in the range of about 15 inches (382 mm) to about 19 inches (484 mm). Preferably, the length of the secondary absorbent 68 is about 17 inches (433 mm).

The width of the secondary absorbent 68 beyond the crotch portion 24 should be at least as wide as the width of the crotch portion 24. The width of the secondary absorbent 68 may be narrowed beyond the crotch portion 24 but may thus compromise the containment of liquid flowing or seeping from the primary absorbent. More preferably, the width outside the crotch portion is wider than in the crotch portion, and is from about 5 inches (127 mm) to about 12 inches (306 mm), alternatively from about 5.5 inches (140 mm) to about 7.5 inches (191 mm). Preferably, the width is about 6.5 inches (165 mm).

Figure 4:
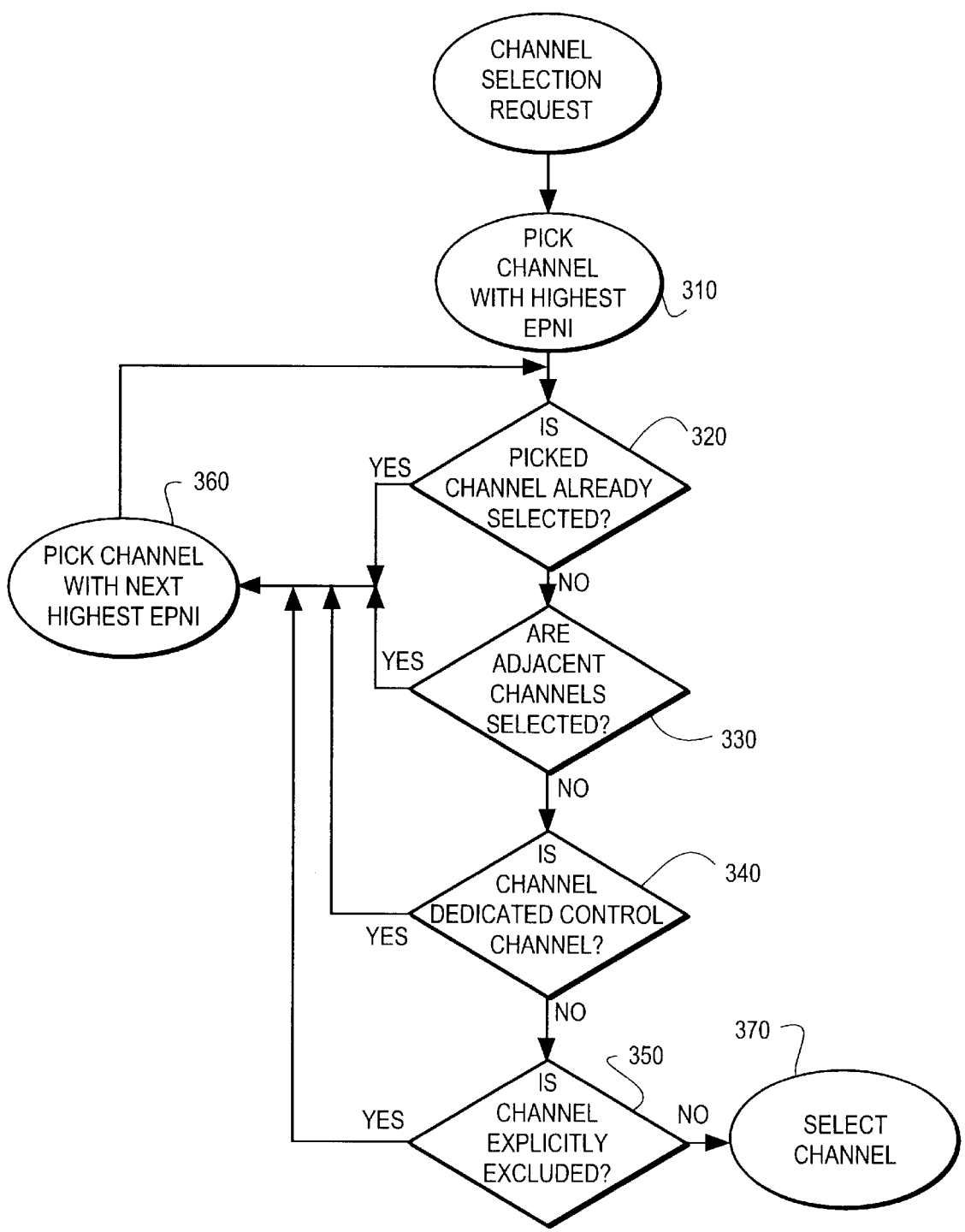
FIG. 4 is a cross section of the garment subassembly taken at 4—4 of FIG. 2.

Referring to FIGS. 2, 3, and 4, the waist elastics 40, the body elastics 64, and the leg elastics 48, 50, are generally covered by the front and back layer elements 19, 21 of the body side layer 14.

Both outer cover layer 12 and body side layer 14 are compliant and soft feeling to the wearer. The following description of materials from which the outer cover layer 12 can be made applies equally to the material of the body side layer 14.

The outer cover layer 12 may be liquid pervious, permitting liquids to readily penetrate into its thickness, or impervious, resistant to the penetration of liquids into its thickness. Outer cover layer 12 may be made from a wide range of materials, such as natural fibers (e.g. wood or cotton fibers), synthetic fibers (e.g. polyester or polypropylene fibers) or from a combination of natural and synthetic fibers or reticulated foams and apertured plastic films. The outer cover layer 12 may be woven, nonwoven or film such as spunbonded, carded, or the like. A suitable outer cover layer 12 is carded, and thermally bonded by means well known to those skilled in the fabric art. Alternatively, the outer cover layer 12 is derived from a spunbonded web. In preferred embodiments, the outer cover layer is spunbonded polypropylene nonwoven with a wireweave bond pattern having a grab tensile of 19 pounds as measured by ASTM D1682 and D1776, a Taber 40 cycle abrasion rating of 3.0 as measured by ASTM D1175 and Handle-O-Meter MD value of 6.6 grams and CD value of 4.4 grams using TAPPI method T402. Such spunbonded material is available from Kimberly-Clark Corporation, Roswell, Ga. The outer cover layer 12 has a weight of from about 0.3 oz. per square yard (osy) to about 2.0 osy, preferably about 0.7 osy.

The position and shape of the leg openings 44, 46 are important to avoid tightness in the crotch and groin area of the wearer, to obtain adequate buttocks coverage, and to prevent the garment 25 from tilting forward, e.g. tilting such that the front waist edge dips lower in relationship to the back waist edge. FIGS. 1 and 2 illustrate the most preferred design for leg fit and buttocks coverage. The shape of the curve across the top of the leg is important. If the curve is too deep, the garment 25 will shift downward and backward resulting in a short front waist, increased back length and bagginess in the seat of the garment. This would cause the garment 25 to appear tilted when worn as evidenced by an unevenness around the waist of the wearer.

Thus the majority of the edge 70 of the front portion of each leg opening 44, 46 is defined by a straight section 72 having a length "L2" at least about 70% of the length "L3" of the entire edge 70. The straight section 72 should form an angle with the centerline A—A of between about 75° and about 100°, and most preferably about 90°. The essentially perpendicular angle formed between the centerline A—A and the front leg, opening is measured using a line extending through the end points of the elastic sections.

With the garment subassembly 10 laid out flat as in FIG. 2, the majority of the edge 74 of the back portion of each leg opening is defined by a straight section 76 having a length "L4" at least about 70% of the length "L5" of the entire edge 74. The straight section 76 forms an acute angle with the longitudinal centerline A—A of the subassembly 10. More preferably, the straight section 76 of the edge 74 forms an acute angle α with the centerline A—A of the garment 25 of between about 50° and 65° and most preferably about 60°. The acute angle is measured using a line extending through the end points of the elastic sections.

The majority of the edge 78 of the crotch portion of each leg opening 44, 46 is defined by a straight section 80 having a length "L6." Preferably, the straight sections 80 are straight for at least about 70% of the entire lengths "L7" of the respective edges 78.

Referring to FIG. 1, each back leg edge portion 74 includes an arcuate section "A1" extending from one end 81 of the respective straight section 76 to a second end 82, thus connecting the respective back leg edge portion to the back end of edge 78 of the respective crotch portion.

Each front leg edge portion 70 includes an arcuate section "A2" extending from one end 84 of the respective straight section 72 to a second end 86 connecting the respective front leg edge portion 70 to the front end of edge 78 of the respective crotch portion.

The shape of the arcuate section "A2" at the inner groin area is important. If the arc is too shallow, tightness may be experienced at the inner groin area.

The preferred narrow crotch width reduces coverage of the buttocks. To compensate for such reduction, the arcuate section "A1" is preferably adjusted toward back waist portion 22, such that the end 82 of the arcuate section "A1" should be positioned slightly forward of centerline B—B as shown in FIGS. 1 and 2.

The waist, back leg, front leg and body elastics 40, 48, 50, 64 respectively are attached to the garment subassembly 10, generally between the outer cover layer 12 and the body side layer 14, using apparatus and processes described hereinafter.

Materials suitable for use as the elastics include a wide variety, but not limited to, of elastic threads, yarn rubber, flat rubber (e.g. as bands), elastic tape, film-type rubber, polyurethane, and, tape-like elastomer, or foam polyurethane or formed elastic scrim. Each elastic may be unitary, multipart, or composite in construction. Threads or ribbons, where used, may be multiple and may be-applied as a composite. The elastomerics used in the elastics may be latent and nonlatent.

Waist elastic 40 is typically about 0.5 inch (13 mm) wide. The elastic may comprise threads, ribbons, a film, or composite. The threads or ribbons may be multiple and may be applied as a composite. Preferably, the waist elastic is threads, more preferably four threads are used as the elastic and the threads are spaced about 0.17 inch (4.3 mm) apart. The threads may be made of any suitable elastomeric material. One suitable material is spandex such as Lycra® threads available from Dupont located in Wilmington, Del. Preferably, suitable waist elastics include threads having a total decitex (g/1000 m) of about 3760 for 0.5 inch (13 mm) wide elastic. The decitex may vary for each element of elastics. Adhesive 55 is used to bond the elastic between the outer cover layer 12 and the body side layer 14. A suitable adhesive includes, for example Findley H2096 hot melt adhesive, available from Findley Adhesives, Milwaukee, Wis.

The leg elastics 48, 50, and crotch elastic 51, including multiple threads in each, are typically about 0.5 inch (13 mm) wide. The elastic may comprise threads, ribbons, a film or composite. The threads, ribbons, etc., may be multiple and may be applied as a composite. The front leg elastics and the crotch elastics may be threads, preferably numbering three threads which are spaced about 0.05 to about 0.50 inch, preferably about 0.10 to about 0.20, more preferably about 0.17 inch (4.3 mm) apart. Back leg elastics numbering up to six threads may have a width of about 0.75 inch (19 mm) and a thread spacing of about 0.05 to about 0.75 inch, preferably about 0.10 to about 0.20, more preferably of about 0.15 inch (3.8 mm) apart. The threads may be made of any suitable elastomeric material. One suitable material is spandex such as Lycra® threads available from Dupont, Wilmington, Del. Preferably, suitable leg elastics include threads having a total decitex (g/1000 m) of about 3760 for a 0.5 inch (13 mm) wide elastic. The decitex may vary for each element of elastics. Adhesive 55 is used to bond the several elastics 48, 50 to the outer cover layer 12, the body side layer 14, and the support sheet 53.

To provide a snug leg fit and to draw up the sides of the crotch portion 24 to a cradle to receive the primary absorbent, the leg elastics 48, 50, and the crotch elastics 51, are elongated when applied to the layers 12 and 14 respectively. Preferably, the leg elastics 48, 50 are applied in multiple segments, with the amount of elongation of each segment while being incorporated into the subassembly 10 being determined according to the position to be occupied by the respective segment. In the case of only front and back leg elastics, the front leg elastics are advantageously elongated less than the back elastics. In the case of front elastics, back elastics, and crotch elastics, the front and crotch elastics are preferably elongated less than the back elastics. Preferably, the elongation of front and crotch elastics are minimal up to between about 100% to about 300%, preferably depending on the decitex of the elastic threads used to about 150% and the elongation of back elastics along the leg openings are minimal to between about 100% to about 300% and preferably depending on the decitex of the elastic threads used to about 250%. The elongations may vary for separate elements and still be within the overall elongation for the composite of elastic elements. The differing tensions allow easier attachment of the primary absorbent pad 66, less tightness in the groin area, and less bunching of the crotch portion 24 caused by high leg elastic retraction. The back leg elastic is under higher elongation to help keep the seat of the garment from creeping up with movement during use. In certain cases, the elongation of the front and back elastics may be minimal when the outer layer is elastic and the front and back elastics are dimensioned to be that of the minimum size of the wearer.

Figure 6:
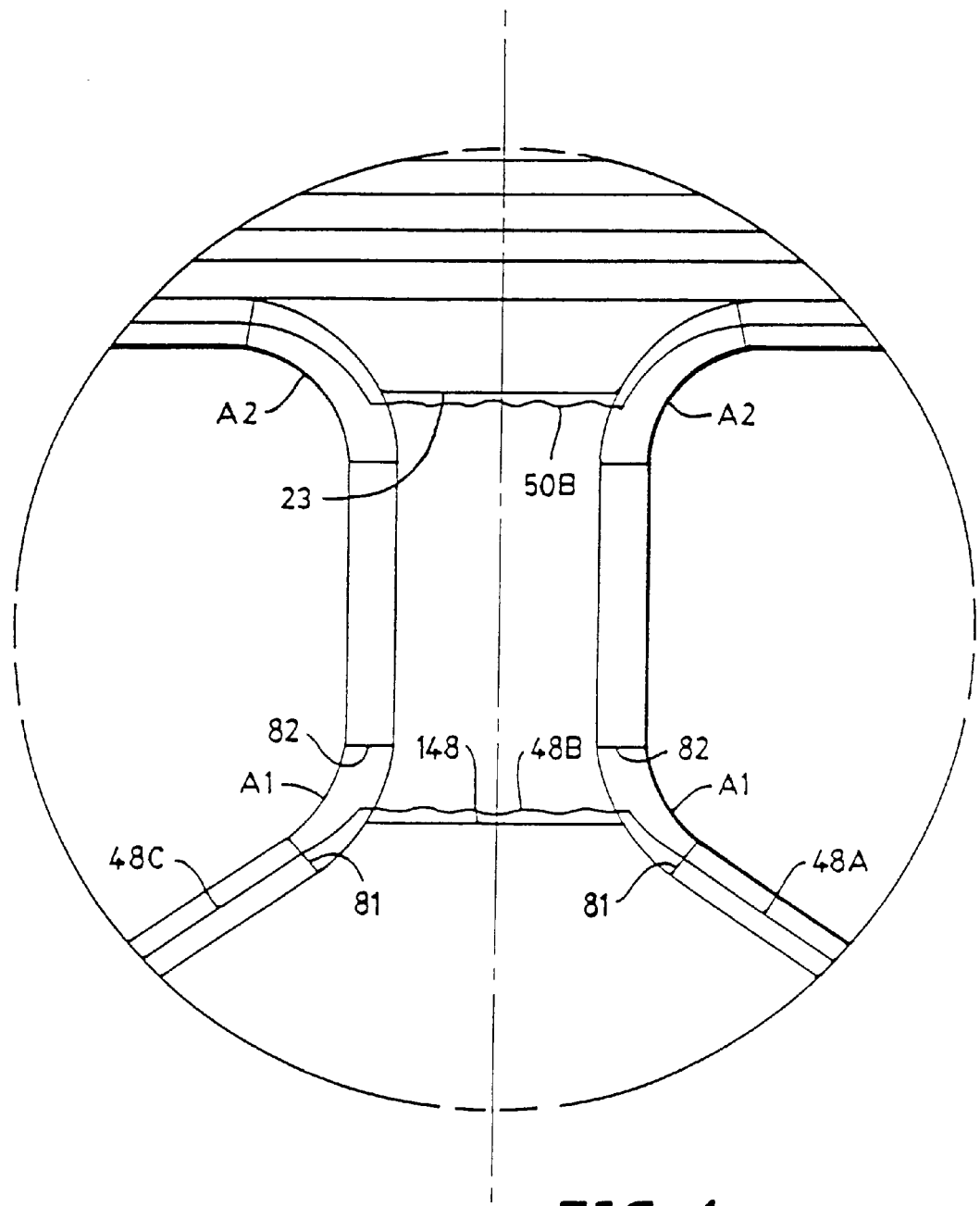
FIGS. 6 and 7 are enlarged cut-away views of a fragment of the subassembly of FIG. 1, showing detail of the cross-crotch elastics.
Figure 7:
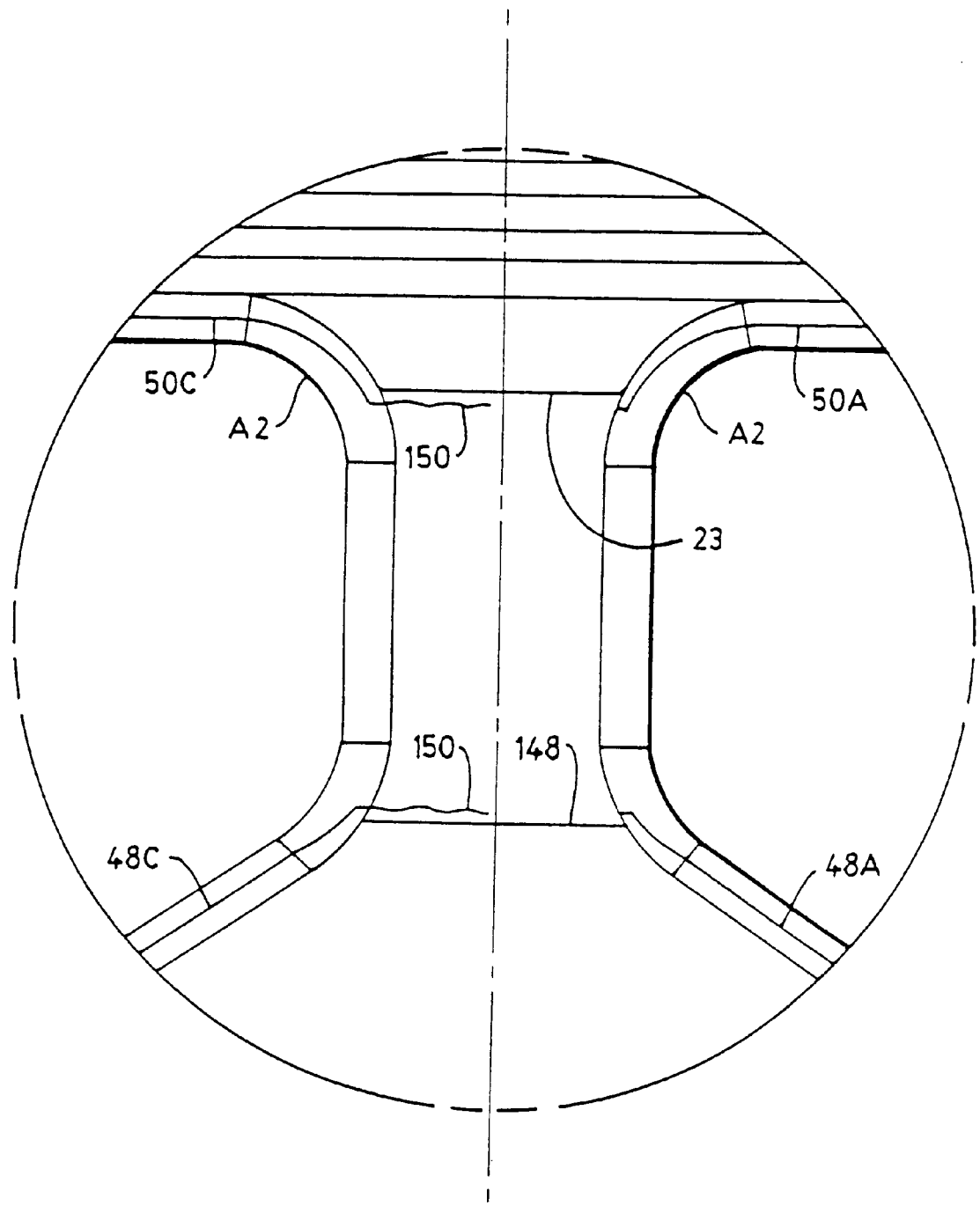

Referring now to FIGS. 1, 6, and 7, the suggested six (back) and three (front) threads of elastic on the respective back and front leg elastics 48 and 50 are each represented as single element of elastic. The following description of the characteristics and use of the single threads applies to the usual multiple threads suggested above.

The composite of the elastics extending about each of the leg openings 44 and 46 comprises a portion of the back leg elastics 48, a portion of the front leg elastics 50, and one of the left and right crotch elastics 51. Referring specifically to FIGS. 1, 6, and 7, the back leg elastic 48 extends, as a first section 48A, from a first locus 92 at or adjacent the edge 28 of the subassembly, width-wise across the subassembly at a substantially consistent acute angle $\alpha$ with the centerline A—A that takes it toward a first edge of the subassembly at front waist portion 18, and generally following the back edge 74 of the leg opening 46 along the straight section 76A and onto the first arcuate section "A1" toward the crotch portion 24, generally terminating in the first arcuate section "A1," at or near the crotch portion 24. Back leg elastic 48 extends, as a second section 48B, from the first arcuate section "A1" across the crotch portion to the second arcuate section "A1." From the second arcuate section "A1," the back leg elastic 48 extends, as a third section 48C, at an acute angle $\alpha$ with the centerline A—A away from the front waist portion 18, and generally following the back edge 74 of the leg opening 44 along the straight section 76B to a second locus 94 at or adjacent edge 34.

In the flat configuration shown for the subassembly in FIGS. 1, 6, and 7, sections 48A and 48C are elongated to between about 100% to about 300%, preferably depending on the decitex of the elastic threads used about 250%, while section 48B is substantially relaxed, and under no substantial elongation. Preferably, section 48B includes a modest amount of slack in the elastic.

The front leg elastic 50 extends, as a first section 50A, from a third locus 96 at or adjacent the side edge 26 of the subassembly width-wise across the subassembly and generally following the front leg edge portion 70 along its longitudinal straight section 72A, and onto the first arcuate section "A2" toward the crotch portion 24, generally terminating in the first arcuate section "A2," at or near the crotch portion 24. Front leg elastic 50 extends, as a second section 50B, from the first arcuate section "A2" across the crotch portion to the second arcuate section "A2." From the second arcuate section "A2," the front leg elastic 50 extends, as a third section 50C, width-wise across the subassembly and generally following the front leg edge portion 70 along its longitudinal straight section 72B to a fourth locus 98 at or adjacent side edge 32. In the flat configuration shown for the subassembly in FIGS. 1, 6, and 7, sections 50A and 50C are elongated to between about 100% to about 300%, preferably depending on the decitex of the elastic threads used about 150%, while section 50B is substantially relaxed, and under no substantial elongation. Preferably, section 50B includes a modest amount of slack in the elastic.

Thus, in the embodiment seen in FIG. 1, the front and rear leg elastics extend across the width W1 of the subassembly 10 as one or more continuous threads.

The crotch elastics 51 extend generally between the back and front leg elastics 48 and 50, with respective ends of the crotch elastics generally being disposed at or near the arcuate sections "A1" and "A2." Accordingly, the properties of the elastics about each leg opening result from the combined contributions of the respective back leg section (e.g. 48A), the respective front leg section (e.g. 50A), and the respective crotch elastic 51.

The reason for providing leg elastics in multiple sections is at least two-fold. First, using multiple sections of elastics facilitates placing of the elastics on the outer cover layer 12 while maintaining advantageous production speeds. As suggested in FIGS. 1, 8, and 9, the subassembly of e.g. FIG. 1 is made as a sequence of such subassemblies in a continuous web 100, with the width "W1"0 of the subassembly disposed in the "with machine" direction of the processing apparatus. In such arrangement, the front and back waist elastics 40, the front and back body elastics 64, and the front and back leg elastics 48, 50 can all be assembled into the subassembly by appropriate continuous feeding of respective continuous threads of elastics into the processing apparatus in the "with machine" direction while the web 100 continuously advances in the "with machine" direction at a constant speed.

Given the orientation of the crotch elastics at essentially 90° to the direction of advance of the web 100, placing the crotch elastics as a portion of a continuous element of either the front or back leg elastics would suggest either (1) momentarily and regularly stopping the advance of the web 100 while the crotch elastic is fed into place, or (2) severely slowing the web 100 and severely driving an elastics guide, in a direction transverse to the web in order to apply the crotch elastic while the web was thus slowed. In either scenario, severe stresses would be placed on the respective drive apparatus, as well as on the web. The invention contemplates, rather, that the crotch elastics are optionally placed in the subassembly 10 as a separate operation placing separate elastics segments, where the crotch elastics segments are first elongated and oriented transverse to the web 100, and are then placed on the web as the web passes the appropriate operating station (not shown) subsequent to placing the leg, body and waist elastics in the subassembly, though the sequence of placing the elastics is not critical.

Referring now to FIGS. 8–11, a first continuous web, which ultimately becomes cover layer 12, is presented against the assembly roll 102 by turning roll 104. A second continuous web, which ultimately becomes body side layer 14, passes under adhesive applicator 106 and over turning rolls 108 and 110, and is pressed against the assembly roll 102 by turning roll 110. Elastic threads 112 are fed from a continuous supply 114 of elastic thread, through feed nip 116, through thread guides 118 and sets of guide fingers 120A and 120B, and between cover layer 12 and body side layer 14 at the nip formed by assembly roll 102 and turning roll 110.

Figure 9:
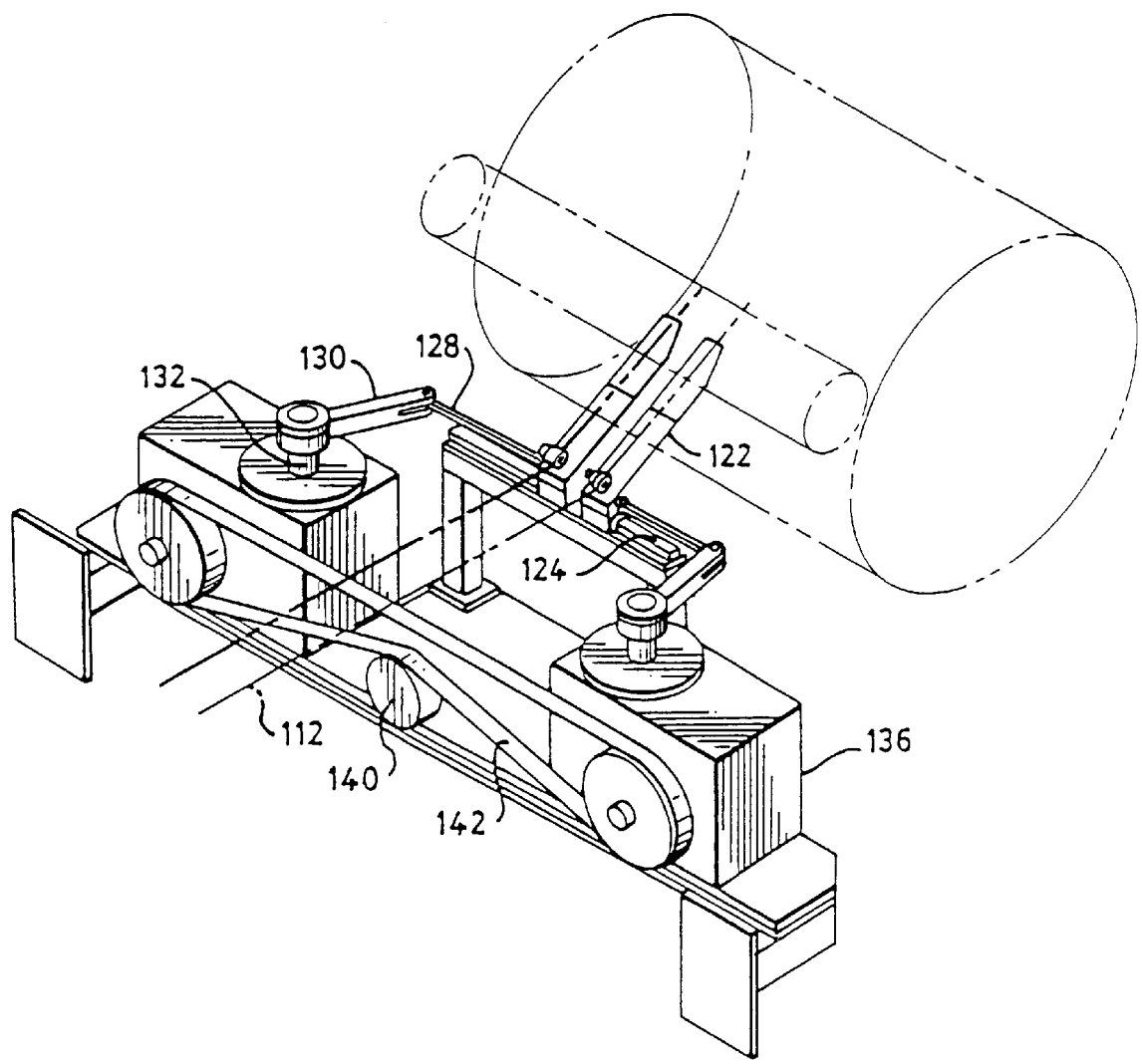
FIGS. 9 and 10 are pictorial views of the nip area of the elevation shown in FIG. 8.
Figure 10:
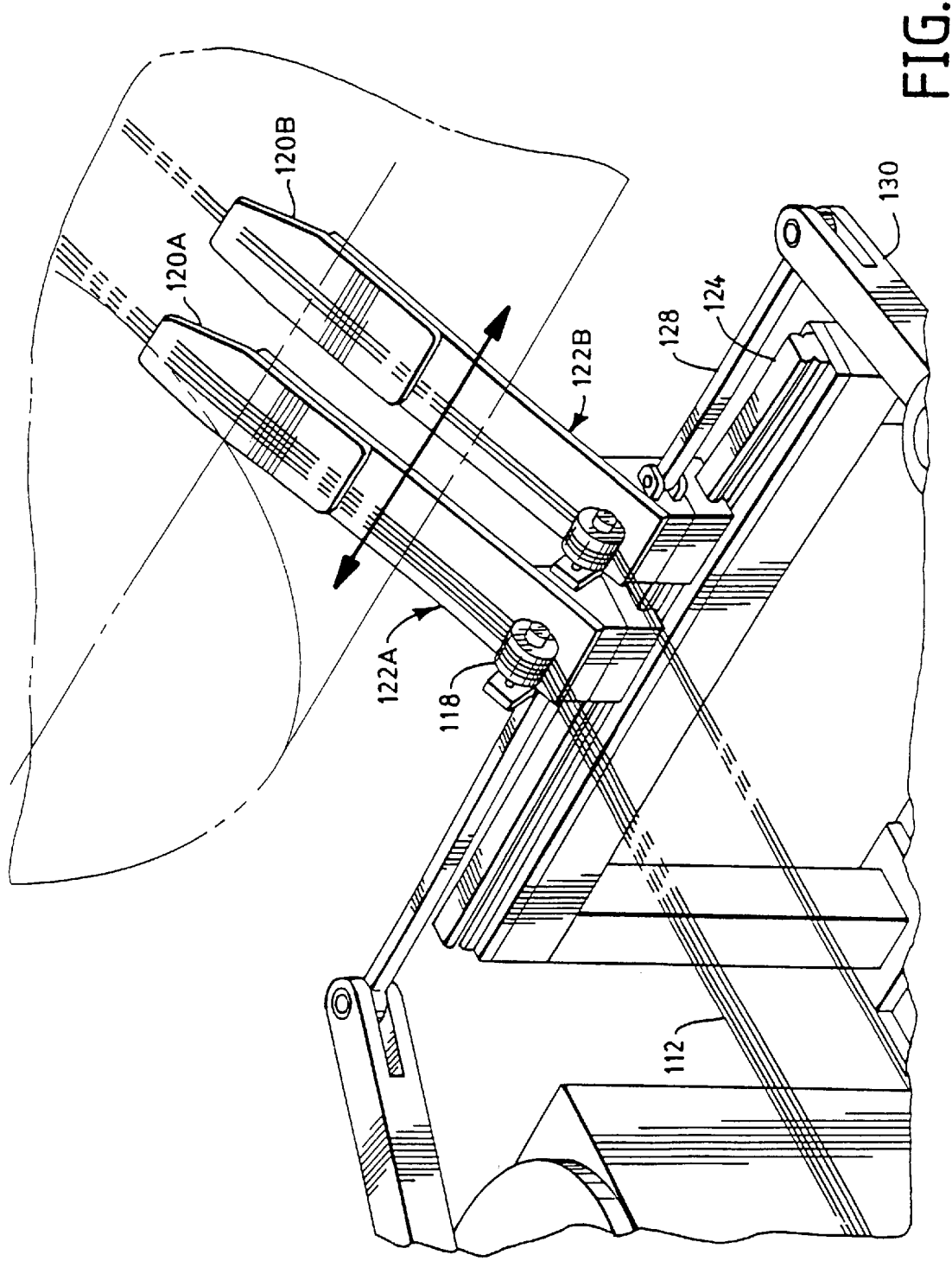

Referring especially to FIGS. 9 and 10, thread guides 118 and corresponding sets of guide fingers 120A and 1208 are elements of lateral guides 122A and 122B respectively. Each of the lateral guides 122A and 1228 is mounted on a transverse slide bar 124 for sliding transverse to the with machine direction of travel of the webs. Each lateral guide 122 is connected to a transverse drive mechanism 136 including linkage arms 128 and 130, vertical drive shaft 132, and a cam follower (not shown). The cam followers follow the corresponding cams inside the respective cam housings. The cams are linked to the machine drive shaft 140 by drive belt 142. Thus, the cams, and correspondingly the thread guides and the sets of guide fingers, move transversely with respect to the with machine direction of the webs as the drive shaft turns. The end result is that rotation of the processing line drive shaft 140 effects transverse motion of the thread guides and the sets of guide fingers, as indicated by the arrows 117 in FIG. 10, in cooperation with the design of the cams and cam followers.

Figure 8:
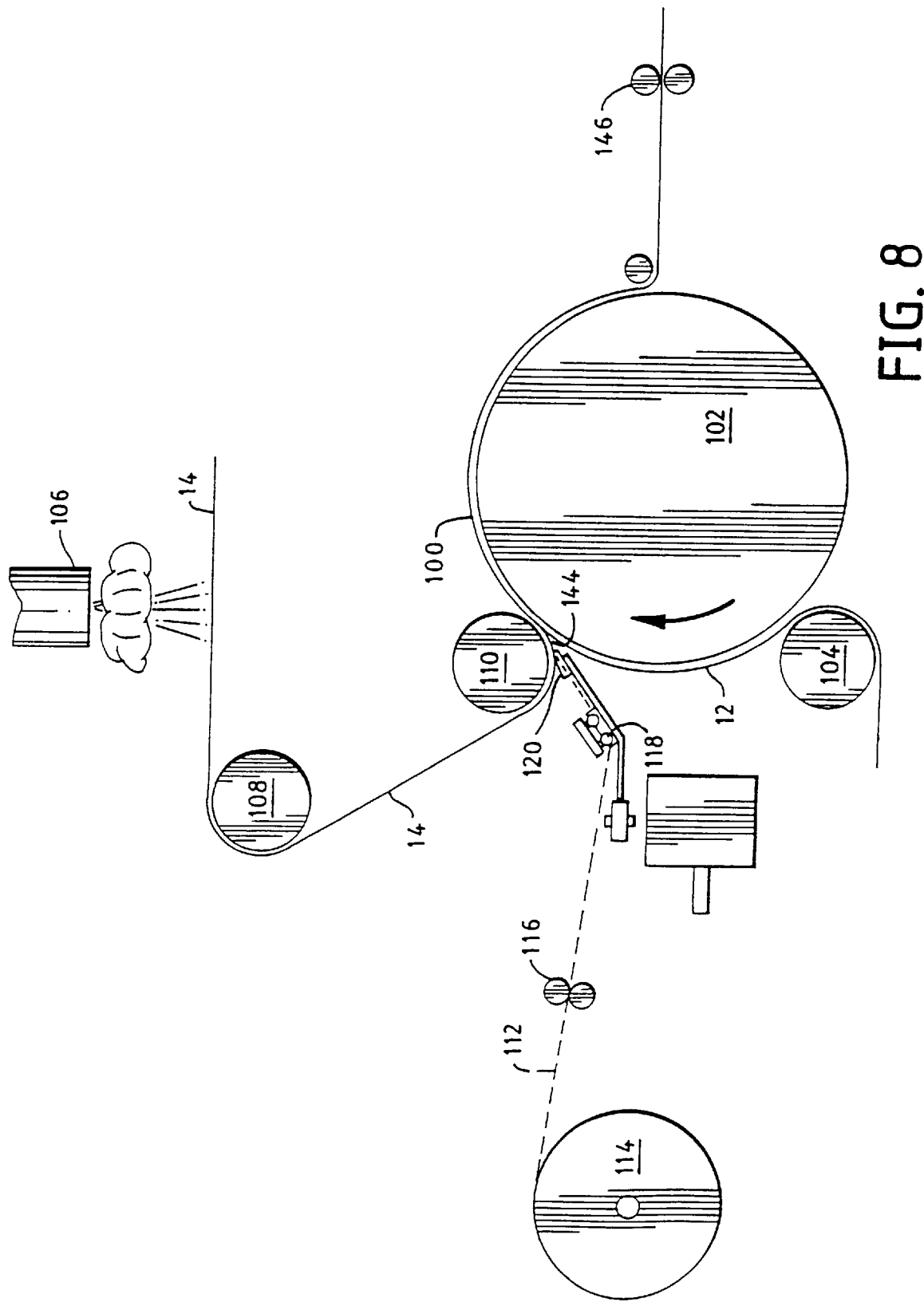
FIG. 8 is a side elevation view of an equipment layout for fabricating and otherwise processing the subassemblies of the invention.

Referring to FIG. 8, the guide fingers 120 are positioned close to the nip 144 so that they closely control the transverse positions of the elastics with respect to the webs 12 and 14 as the webs 12 and 14 enter the nip 144 and correspondingly trap the elastics between them, fixing the position of the elastics between them by means of adhesive 55 as shown in FIG. 3. Accordingly, the guide fingers 120 are preferably physically positioned, and provide guidance to the threads of elastic, within two inch of the nip 144. To the extent the fingers can be placed closer to the nip 144, they provide more positive guidance to the elastic. By careful design of the guide fingers 120, and by careful control of the positioning of the guide fingers 120 with respect to nip 144, the guide fingers 120 can be advantageously positioned within two inches, advantageously within 0.75 inch of the line of contact defined at the nip between roll 102 and 110. Additionally, body elastics 64 and waist elastics 40 can be incorporated at nip 144 in the conventional manner of providing stationary feeds and guides at the nip.

The limitation on how close the guide fingers 120 can be placed to the nip is controlled by the ability to design fingers which can affirmatively guide the threads of elastic while avoiding having the fingers themselves drawn into the nip. The criticality of urging the fingers as ultimately close as possible to the nip can be attenuated by directing the threads 112 onto the adhesive-coated layer 14 ahead of nip 144, preferably instantaneously ahead of the nip 144, as suggested by the depiction in FIG. 8. By directing the threads of elastic onto layer 14 ahead of the nip, the open distance spanned by the threads between the fingers 120 and the adhesive-coated layer 14 is minimized, being held to less than 0.5 inch, for example 0.25–0.375 inch (6 mm to 10 mm).

Figure 11:
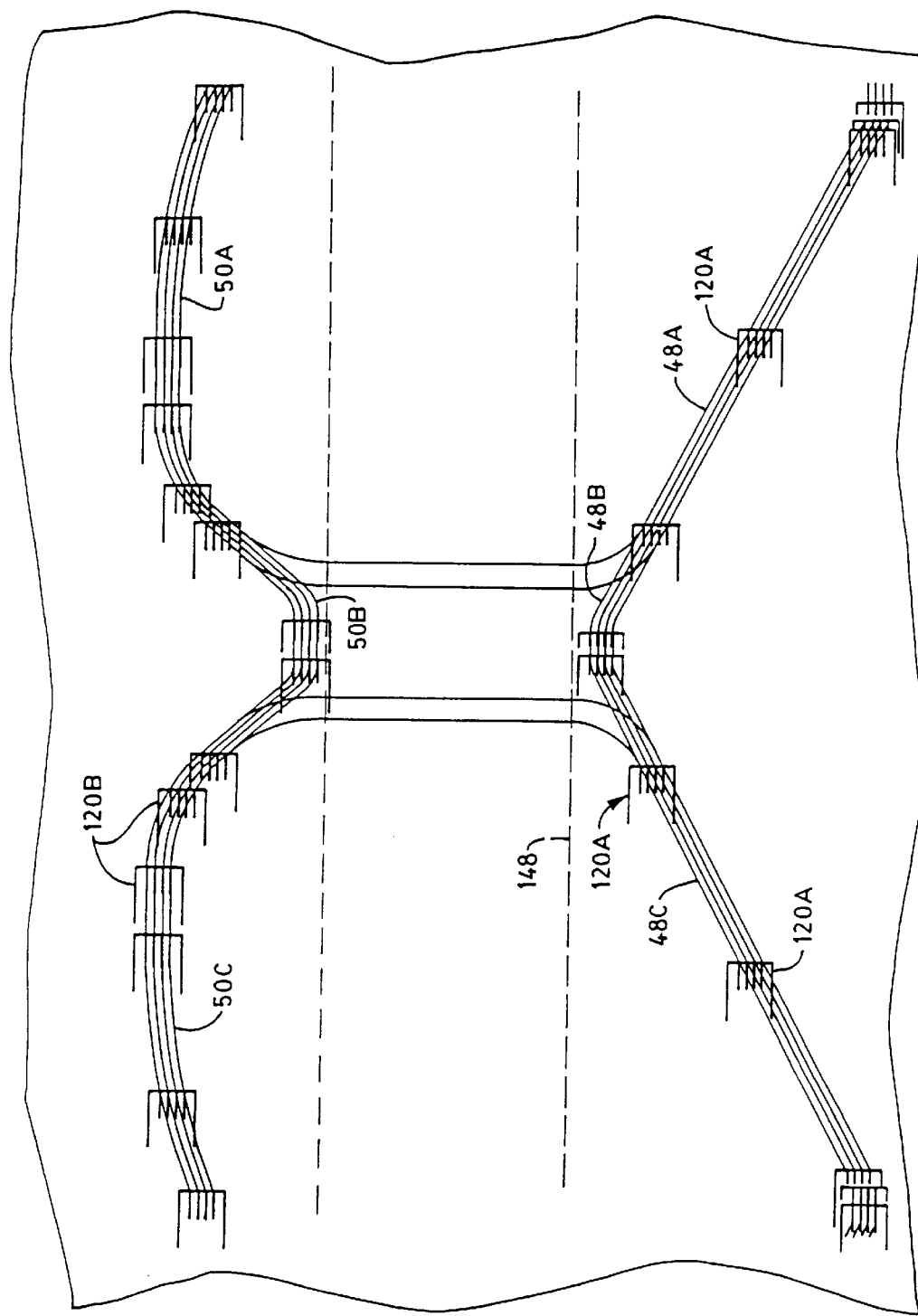
FIG. 11 is a plan view showing the relative transverse positioning of the front and back leg elastics along the advancing web while the outer cover layer and body side layer are being joined.

The transverse movement of the lateral guides 122, and thus fingers 120, as the webs advance along the processing line, creates transverse positioning of the elastics threads 112 with respect to the with machine direction of the advancing webs 12 and 14. FIG. 11 shows the pattern of transverse movement of the sets of guide fingers 120A and 120B relative to the movement of the web in the with machine direction, along the processing line. In FIG. 11, the sets of fingers 120A and 120B are depicted at several locations along the front and back edges of the leg openings 44, 46, to indicate that it is the positioning of the sets of fingers 120A and 120B, and the dynamic changing of that positioning by the drive mechanism 126, that determines the instantaneous transverse location of the elastics in the web at any point and time while the elastics are being placed in the web at nip 144 as shown in FIGS. 8–11. Comparing FIGS. 1, 10, and 11, it is seen that the set of fingers 120A generally places the threads of the back leg elastics generally parallel to each other in the web, while the set of fingers 120B generally places the threads of the front leg elastics generally parallel to each other in the web, both along their respective portions of the designed paths defining the front 70 and back 74 edges of the leg openings 44 and 46.

Figure 13:
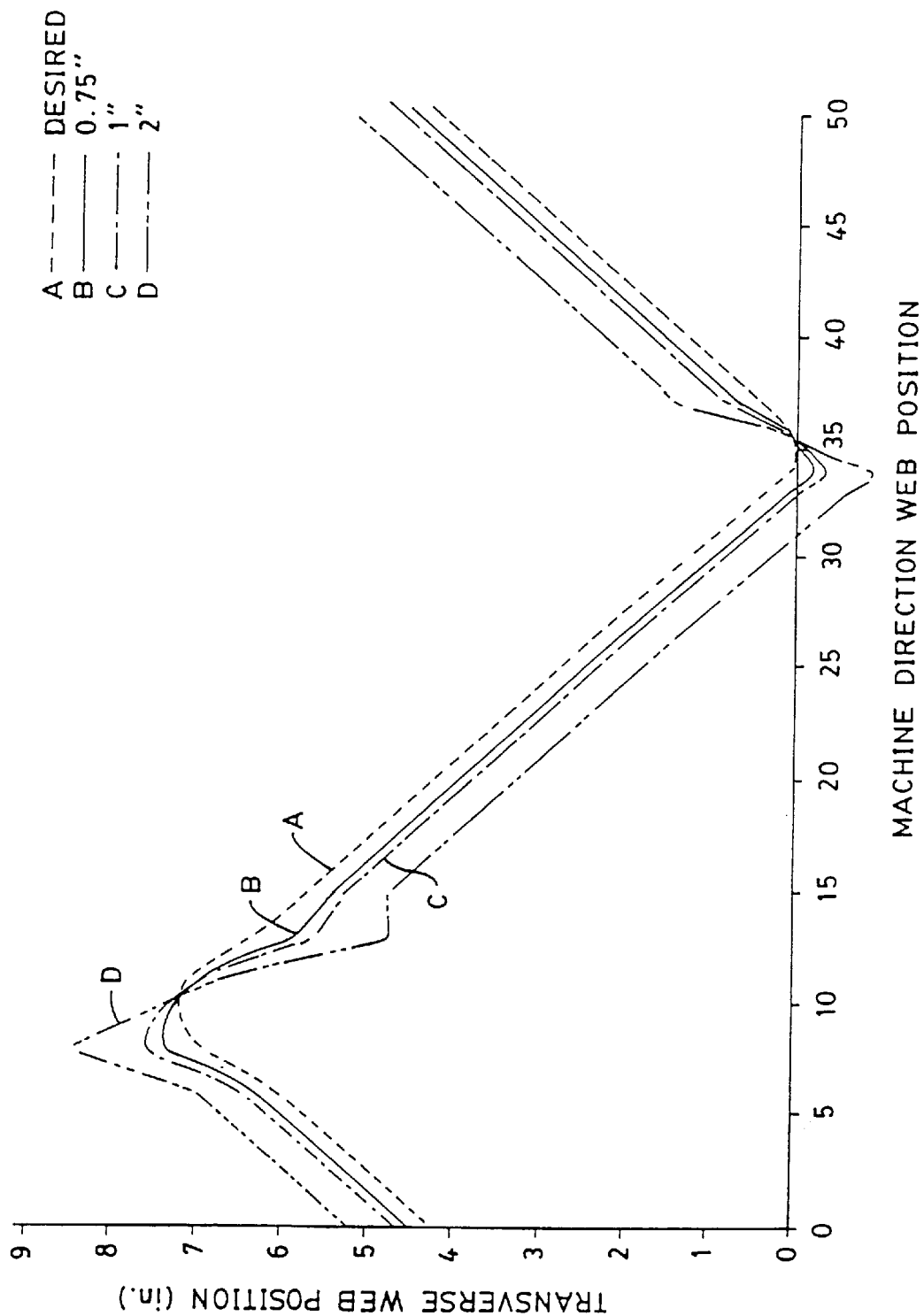
FIG. 13 is a diagram illustrating the elastic guide movement required to attain a given pattern in the final product for various guide to nip distanes.
Figure 1:
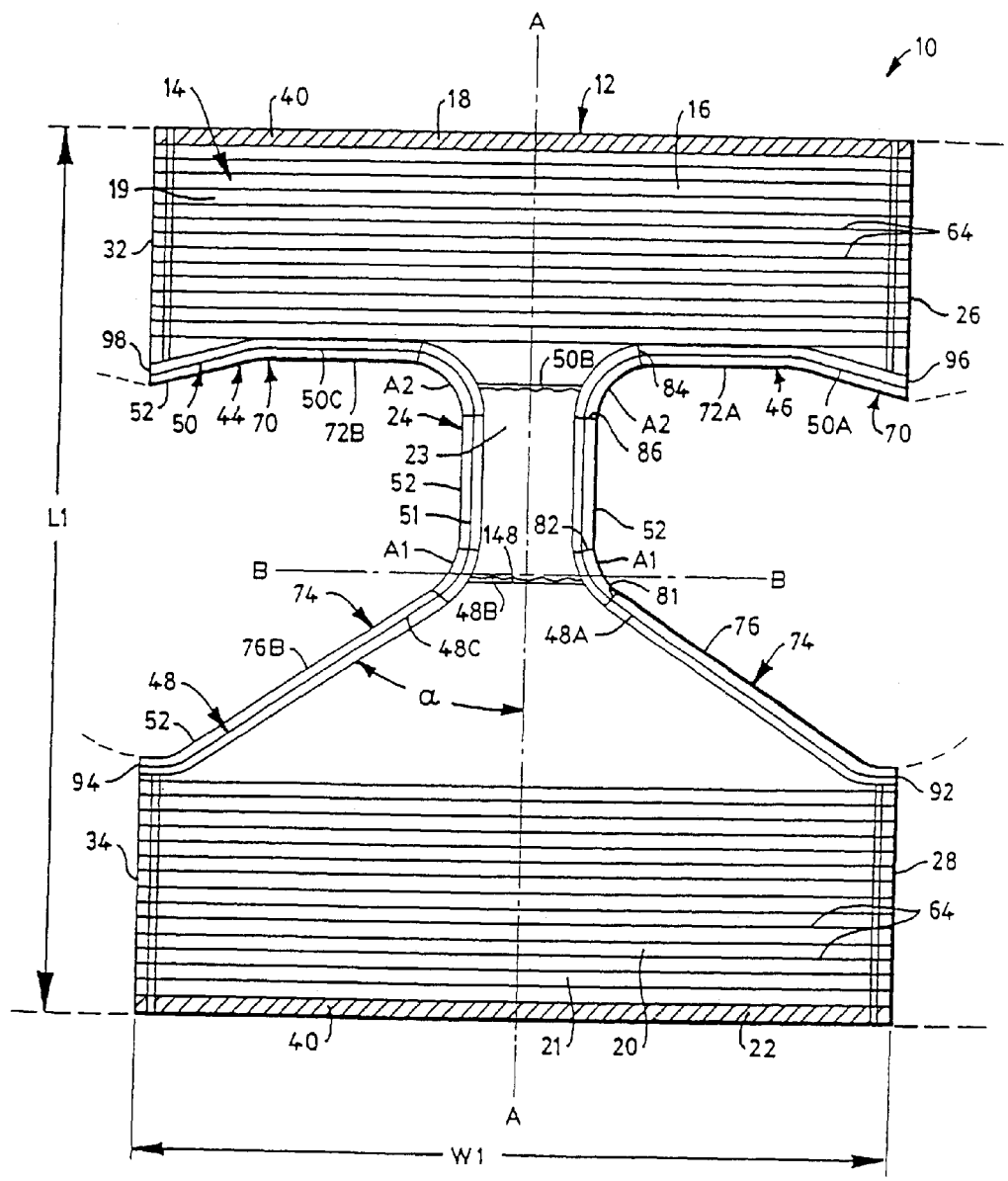
Figure 2:
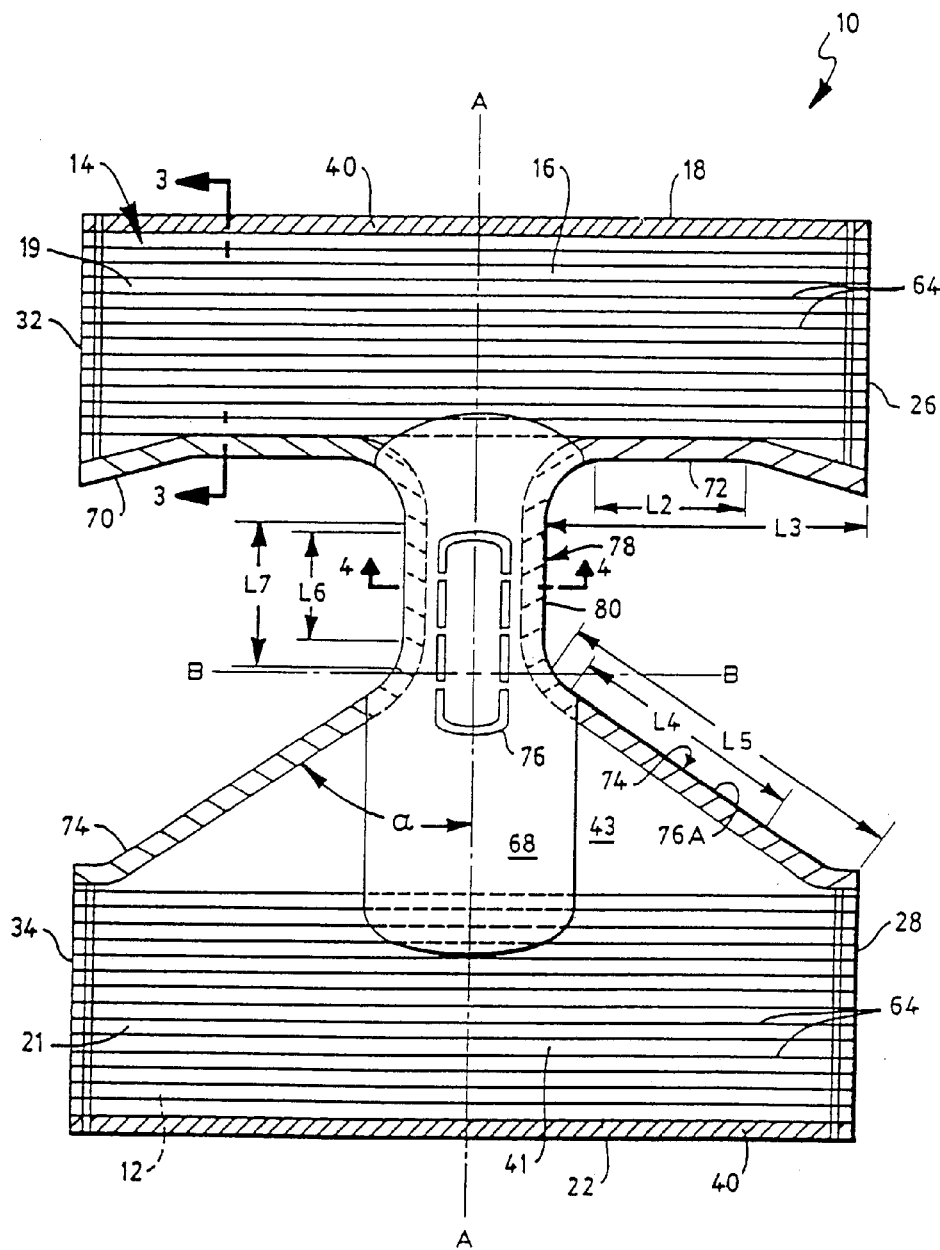
Figure 3:
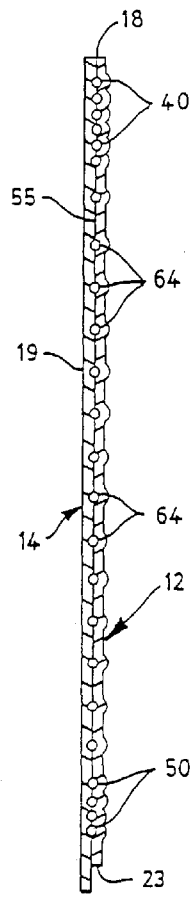
Figure 4:
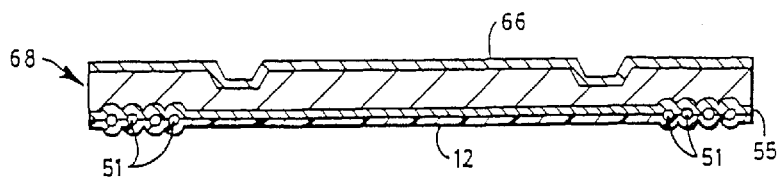

FIG. 13 is a diagram of the transverse movement required of guide 122, in order to produce a given elastic thread pattern, given three different guide to nip distances. FIG. 13 illustrates that because of the gap between the elastic guide and the nip, the elastic guide movement never matches the required elastic pattern. The curves B, C, and D show that for a given elastic pattern, the guide movement amplitude and rates of change increase and become progressively more tortuous as the distance from the guide to the nip increases. Large, abrupt changes in guide movement cause shock and vibration and thus are deleterious to machinery. Therefore, it is advantageous to keep the guide as close to the nip as possible.

The threads of elastic deviate slightly from their parallel relationships with each other as the elastic threads traverse paths that deviate from the with machine direction, the distance between the threads 90 being generally constant as they emerge from the fingers 120. Such deviations from the parallel, resulting from the cross machine traverse of the elastics, are included herein within the phrase "generally parallel" as respects the relationships of the threads of elastic to each other.

It will be understood that FIG. 11 represents only one garment in the continuous sequence of garment subassemblies 10 contained in the web 100 passing through nip 144. It will also be understood that the web passing through the nip 144 is further acted upon at cutter 146 as shown in FIG. 8 to cut away material from the web 100 in creating the leg openings 44 and 46.

In general, then, webs 12 and 14 are provided as substantially endless rolls from unwind stands (not shown). Web 14 is typically provided as front and back layer elements 19 and 21. Space 23 separates the elements 19 and 21, and generally corresponds with the central area of the crotch portion and the portion of the web 12 which is cut out to form leg openings 44 and 46. Adhesive 55 is applied to the front and back elements 19 and 21 of web 14 by adhesive applicator 106. Webs 12 and 14 are joined adhesively, with elastic threads being interposed between webs 12 and 14 at nip 144, and with space 23 interposed between the front and back elements 19, 21 of the body side layer 14. The transverse positions of the elastics change according to a pre-set path of transverse movements, driven by the drive shaft 140 which drives and times the several operations along the processing line. The threads of elastic 112, as placed by the guide fingers 120, traverse respective paths that ultimately follow the front and back edges of the leg openings 44 and 46, as defined at cutter 146, in registration with the advance of the web, and accordingly, with the advance of the series of garment subassemblies 10 being defined in the web at nip 144 and cutter 146. The portions of the threads of elastic located along the front and back edges of the leg openings are stretched. The portions traversing the crotch portion are substantially relaxed. The crotch portions of the elastic are separately placed in the subassembly 10 at a later processing station, preferably downstream from the cutter 146.

Figure 12:
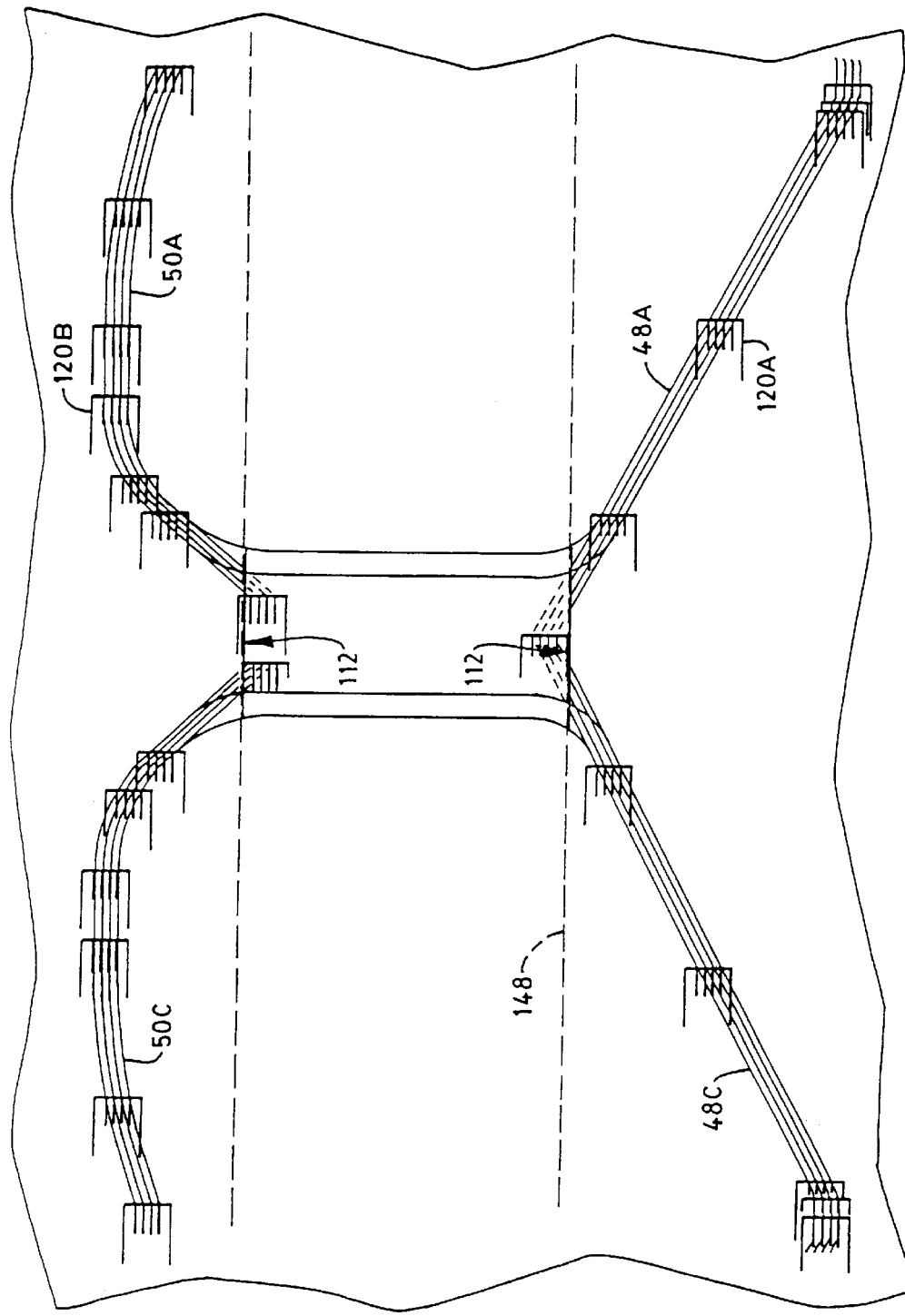
FIG. 12 is a plan view as in FIG. 11, showing an alternate pattern for the elastic threads.

A second embodiment of the subassembly is illustrated in FIG. 12. In the second embodiment, the front edge 148 of back layer element 21 is disposed rearwardly of that same edge 148 as depicted in the embodiment of FIG. 11, while the guide fingers 120A traverse the same path as in FIG. 11. Accordingly, as the threads of elastic 112 extend across the crotch portion 24, the threads 112 are guided forwardly of edge 148, into unsecured space 23, and are thus not held between the layers 12 and 14, and are not controlled by the adhesive on layer 14. Rather, the tension is maintained on the threads of elastic 112 across the crotch portion 24, such that the threads retract along the edge 148 of the layer element 21 in a configuration that loosely resembles a rope under tension. The rope or the at least one elastic strand of the rope is subsequently cut such that the cut portions of the threads retract to positions generally defined by the intersection of the edge 148 of the back layer element and the path of the threads adhesively held between layer and the back layer element. Thus, the at least one cut threads 112 generally include loose intermediate ends 150 after being cut, as shown in FIG. 7.

The front layer element 19 is applied along the back edge 178 of the leg opening in a manner similar to the application of the back layer element 21.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. A garment blank subassembly having a front body portion, a back body portion, and a crotch intermediate of and extending from the front body portion to the back body portion and between a pair of leg openings in a garment to be assembled from the garment blank subassembly, the front body portion having first and second front leg edge portions along the leg openings, a front end opposite the first and second front leg edge portions, and first and second front sides, the back body portion having first and second back leg edge portions along the leg openings, a back end opposite the first and second back leg edge portions, and first and second back sides, the crotch having first and second crotch edge portions on opposing sides thereof along the leg openings, the garment blank subassembly having a length extending between the front and back ends, a width extending between the first and second sides, and a longitudinal centerline between the first and second front and back sides, each of the first and second back leg edge portions having an angular portion extending generally along a line forming an acute angle with the longitudinal centerline, the garment blank subassembly, when laid out flat, comprising:

(a) a first layer, extending from the first end through the crotch to the second end;

(b) a first elastic attached to the first layer, and extending from a first locus adjacent the first back side, as a first section of the first elastic, along the width of the garment blank subassembly, toward the front end at an acute angle with the longitudinal centerline and generally following the first back leg edge portion toward the crotch, as a second section of the first elastic across the crotch, and as a third section of the first elastic away from the first end at an acute angle with the longitudinal centerline and generally following the second back leg edge portion, to a second locus adjacent the second back side, the first and third sections of the first elastic being stretched and the second section of the first elastic being substantially relaxed when the garment blank subassembly is laid out flat; and (c) a second layer, the first abnd third sections of the first elastic being disposed between the first and second layers.

2. A garment blank subassembly as in claim 1, the second layer comprising a body side liner having a front layer element attached to the front portion of the first layer, and a back layer element attached to the back portion of the first layer, and including an unsecured space between the front layer element and the back layer element.

3. A garment blank subassembly as in claim 2, the first and third sections of the first elastic being secured between the first and second layers, the second section of the first elastic being disposed in the unsecured space.

4. A garment blank subassembly as in claim 3, the second section of the first elastic being attached to at least one of the first and second layers.

5. A garment blank subassembly as in claim 3, the second section of the first elastic being attached to at least one of the first and second layers, and including a third elastic attached in said garment blank subassembly along the first crotch edge portion and a fourth elastic attached in said garment blank subassembly along the second crotch edge portion, said third and fourth elastics extending in a direction generally corresponding to the direction of the longitudinal centerline.

6. A garment blank subassembly as in claim 5, wherein the third and fourth elastics are stretched when the garment blank subassembly is laid out flat.

7. A garment blank subassembly as in claim 6, wherein the first and third sections of the first elastic comprise arcuate portions, each arcuate portion having a first end attached in said garment blank subassembly at the end of the respective first angular portion and a second end attached in said garment blank subassembly at the joinder of the respective back leg edge portion with the respective first and second crotch edge portions, and wherein the second section of the first elastic extends across the crotch between the second ends of the first arcuate portions.

8. A garment blank subassembly as in claim 7, the second section of the first elastic being severed in at least one location.

9. A garment blank subassembly having a front body portion, a back body portion, and a crotch intermediate of and extending from the front body portion to the back body portion and between a pair of leg openings in a garment to be assembled from the garment blank subassembly, the front body portion having first and second front leg edge portions along the leg openings, a front end opposite the first and second front leg edge portions, and first and second front sides, the back body portion having first and second back leg edge portions along the leg openings, a back end opposite the first and second back leg edge portions, and first and second back sides, the crotch having first and second crotch edge portions on opposing sides thereof along the leg openings, the garment blank subassembly having a length extending between the front and back ends, a width extending between the first and second sides, and a longitudinal centerline between the first and second front and back sides, each of the first and second back leg edge portions having an angular portion extending generally along a line forming an acute angle with the longitudinal centerline, the garment blank subassembly, when laid out flat, comprising:

(a) a first layer, extending from the first end through the crotch to the second end; and (b) a first elastic attached in said garment blank subassembly, and extending from a first locus adjacent the first back side, as a first section of the first elastic, along the width of the garment blank subassembly, toward the front end at an acute angle with the longitudinal centerline and generally following the first back leg edge portion toward the crotch, as a second section of the first elastic across the crotch, and as a third section of the first elastic away from the first end at an acute angle with the longitudinal centerline and generally following the second back leg edge portion, to a second locus adjacent the second back side, the second section of the first elastic being severed in at least one location.

10. A garment blank subassembly having a front body portion, a back body portion, and a crotch intermediate of and extending from the front body portion to the back body portion and between a pair of leg openings in a garment to be assembled from the garment blank subassembly, the front body portion having first and second front leg edge portions along the leg openings, a front end opposite the first and second front leg edge portions, and first and second front sides, the back body portion having first and second back leg edge portions along the leg openings, a back end opposite the first and second back leg portions, and first and second back sides, the crotch having first and second crotch edge portions on opposing sides thereof along the leg openings, the garment blank subassembly having a length extending between the front and back ends, a width extending between the first and second sides, and a longitudinal centerline between the first and second front and back sides, each of the first and second back leg edge portions having an angular portion extending generally along a line forming an acute angle with the longitudinal centerline, the garment blank subassembly, when laid out flat, comprising:

(a) a first layer, extending from the first end through the crotch to the second end;

(b) a first elastic extending from a first locus adjacent the first front side, as a first section of the first elastic, along the width of the garment blank subassembly and generally following the first front leg edge toward the crotch at an angle essentially perpendicular to the longitudinal centerline, as a second section of the first elastic across the crotch, and as a third section of the first elastic along and generally following the second front leg edge portion at an angle essentially perpendicular to the longitudinal centerline to a second locus adjacent the second front side; and (c) a second layer, the first and third sections of the first elastic being attached to at least one of the first and second layers, the second layer comprising a body side liner having a front layer element attached to the front portion of the first layer, and a back layer element attached to the front portion of the first layer, and including an unsecured space between the front layer element and the back layer element, the second section of the first elastic being disposed in the unsecured space.

11. A garment blank subassembly as in claim 10 wherein the second section of the first elastic is attached to at least one of the first and second layers.

12. A garment blank subassembly as in claim 11, including a third elastic attached in said garment blank subassembly along the first crotch edge portion and a fourth elastic attached in said garment blank subassembly along the second crotch edge portion, said third and fourth elastics extending in a direction generally corresponding to the direction of the longitudinal centerline.

13. A garment blank subassembly as in claim 12, wherein the third and fourth elastics are stretched when the garment blank subassembly is laid out flat.

14. A garment blank subassembly as in claim 13, the first and third sections of the first elastic comprising first arcuate portions, each arcuate portion having a first end attached in said garment blank subassembly at the end of the respective first essentially perpendicular portion and a second end connecting the respective front leg edge portion to the respective crotch edge portion, and wherein the second section of the first elastic extends across the crotch between the second ends of the first arcuate portions.

15. A garment blank subassembly as in claim 13, the second section of the first elastic being severed in at least one location.

16. A garment blank subassembly having a front body portion, a back body portion, and a crotch intermediate of and extending from the front body portion to the back body portion and between a pair of leg openings in a garment to be assembled from the garment blank subassembly, the front body portion having first and second front leg edge portions along the leg openings, a front end opposite the first and second front leg edge portions, and first and second front sides, the back body portion having first and second back leg edge portions along the leg openings, a back end opposite the first and second back leg edge portions, and first and second back sides, the crotch having first and second crotch edge portions on opposing sides thereof along the leg openings, the garment blank subassembly having a length extending between the front and back ends, a width extending between the first and second sides, and a longitudinal centerline between the first and second front and back sides, each of the first and second back leg edge portions having an angular portion extending generally along a line forming an acute angle with the longitudinal centerline, the garment blank subassembly, when laid out flat, comprising:

(a) a first layer, extending from the first end through the crotch to the second end;

(b) a first elastic extending from a first locus adjacent the first back side, as a first section of the first elastic, along the width of the garment blank subassembly, and generally following the first back leg edge portion toward the crotch, as a second section of the first elastic extensible across the crotch, and as a third section of the first elastic along and generally following the second back leg edge portion to a second locus adjacent the second back side, the second section of the first elastic being substantially relaxed when the garment blank subassembly is laid out flat; and (c) a second elastic extending from a third locus adjacent the first front side, as a first section of the second elastic, along the width of the garment blank subassembly and generally following the first front leg edge portion toward the crotch, as a second section of the second elastic extensible across the crotch, and as a third section of the second elastic away from the first end and generally following the second back leg edge portion, to a fourth locus adjacent the second front side, the second section of the second elastic being substantially relaxed when the garment blank subassembly is laid out flat, the second sections of the first and second elastics being severed in at least one location.

17. A garment blank subassembly as in claim 16, the second sections of the first and second elastics being disposed in the unsecured space.

18. A garment blank subassembly as in claim 17, the second section of the first elastic being attached to at least one of the first and second layers and the second section of the second elastic being attached to at least one of the first and second layer.

19. A garment blank subassembly as in claim 18, including a third elastic attached to at least one of the first and second layers along the first crotch edge portion and a fourth elastic attached to at least one of the first and second layers along the second crotch edge portion.

20. A garment blank subassembly as in claim 19, wherein the third and fourth elastics are stretched when the garment blank subassembly is laid out flat.

21. A garment blank subassembly as in claim 20, the first section of the first elastic comprising a first arcuate portion having a first end disposed at the end of the first angular portion and a second end disposed at the joinder of the back leg edge portion with the first crotch edge portion, the third section of the first elastic comprising a second arcuate portion having a first end disposed at the end of the second angular portion and a second end disposed at the joinder of the back leg edge portion with the second crotch edge portion, and wherein the second section of the first elastic is extensible across the crotch between the second end of the first arcuate portion and the second end of the second arcuate portion, the first section of the second elastic comprising a third arcuate portion having a first end disposed at the end of the second angular portion and a second end disposed at the joinder of the front leg edge portion with the first crotch edge portion, and the third section of the second elastic comprising a fourth arcuate portion having a first end disposed at the end of the first essentially perpendicular angle portion and a second end disposed at the joinder of the front leg edge portion with the second crotch edge portion, and wherein the second section of the first elastic is extensible across the crotch between the second end of the third arcuate portion and the second end of the fourth arcuate portion.

22. A garment blank subassembly as in claim 21, the second sections of the first and second elastics being severed in at least one location.

23. A garment blank subassembly as in claim 22, including a third elastic attached in the garment blank subassembly along the first crotch edge portion and a fourth elastic attached in the garment blank subassembly along the second crotch edge portion.

24. A garment blank subassembly as in claim 23, wherein the third and fourth elastics are stretched when the garment blank subassembly is laid out flat.

* * * * *

UNITED STATES PATENT AND TRADEMARK OFFICE
CERTIFICATE OF CORRECTION

PATENT NO.    : 6,098,203
DATED         : August 8, 2000
INVENTOR(S)   : Gregory John Rajala, Steven Craig Gehling and Paul Daniel Suke It is certified that error appears in the above-identified patent and that said Letters Patent is hereby corrected as shown below:

Title page,
Should be deleted and substitute therefor the attached title page.

Drawings,
Please delete Figures 1-4, and replace them with the attached Figures 1-4.

Column 6,
Line 2, change "an" to -- a --;
Line 29, change "distanes" to -- distances --.

Column 16,
Line 43, change "abnd" to -- and --.

Signed and Sealed this

Sixteenth Day of July, 2002

Attest:

JAMES E. ROGAN
Attesting Officer   Director of the United States Patent and Trademark Office

United States Patent [19]

Rajala et al.

[11] Patent Number: 6,098,203
[45] Date of Patent: Aug. 8, 2000

[54] DISPOSABLE GARMENT AND RELATED MANUFACTURING EQUIPMENT AND METHODS

[75] Inventors: Gregory John Rajala, Neenah; Steven Craig Gehling, Oshkosh; Paul Daniel Suke, Appleton, all of Wis.

[73] Assignee: Kimberly-Clark Worldwide, Inc., Neenah, Wis.

[21] Appl. No.: 08/959,622

[22] Filed: Oct. 28, 1997

Related U.S. Application Data

[63] Continuation of application No. 08/382,108, Jan. 31, 1995, Pat. No. 5,745,922.

[51] Int. Cl.$^7$ ........................................... A41B 9/00
[52] U.S. Cl. ........................ 2/401; 2/111; 2/243.1; 2/403; 2/406; 604/385.2; 604/396
[58] Field of Search ..................... 2/111, 400, 401, 2/402, 406, 403; 604/358, 385.1, 385.2, 394, 396

[56] References Cited

U.S. PATENT DOCUMENTS

| | | | |
|---|---|---|---|
| 2,581,904 | 1/1952 | Burns | 2/111 |
| 3,488,778 | 1/1970 | Goujon et al. | 2/111 |
| 3,560,292 | 2/1971 | Butter | 2/111 |
| 3,599,640 | 8/1971 | Larson | 128/286 |
| 4,205,679 | 6/1980 | Repke et al. | 128/287 |
| 4,610,680 | 9/1986 | Lafleur | 604/385 |
| 4,619,649 | 10/1986 | Roberts | 604/396 |
| 4,743,241 | 5/1988 | Igaue et al. | 604/385 |
| 4,960,414 | 10/1990 | Meyer | 604/395 |
| 5,080,741 | 1/1992 | Nomura et al. | 156/201 |
| 5,163,932 | 11/1992 | Nomura et al. | 604/385.2 |

*Primary Examiner*—John J. Calvert
*Assistant Examiner*—Katherine Moran
*Attorney, Agent, or Firm*—Michael L. Winkelman

[57] ABSTRACT

This invention pertains to a three dimensional disposable garment, subassemblies of the garment, and apparatus and methods for making the garment and subassemblies. The garment is designed to hold a primary absorbent sanitary pad. The garment may have elasticized leg and waist openings and be stretchable about the hip and stomach regions of a user. The garment provides backup protection to control egress of fluids that leak or seep around or through the primary sanitary pad. The garment includes a secondary absorbent positioned in the crotch area and extending into the body of the disposable garment, front and back, and preferably over the leg elastics to trap, inside the garment, leakage from the primary absorbent, and to prevent strike through onto e.g. outer clothing and bed linen. The apparatus and methods facilitate assembling leg elastics and crotch elastics into the garment subassemblies while assembling a series of garment subassemblies in a continuous web structure at a constant, or relatively constant, continuous and efficient speed.

24 Claims, 13 Drawing Sheets

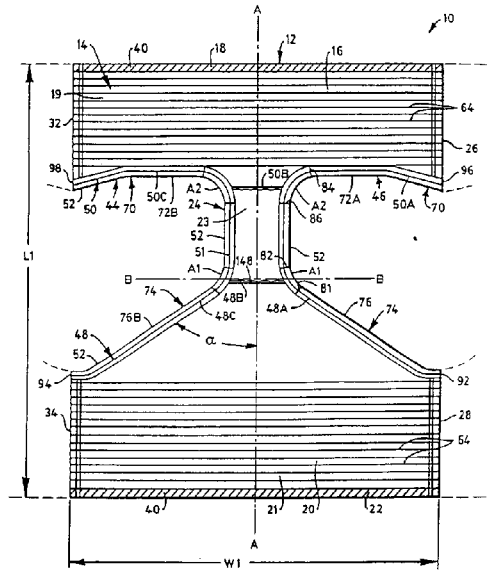

US006098203C1

(12) EX PARTE REEXAMINATION CERTIFICATE (10278th)

United States Patent
Rajala et al.

(10) Number: US 6,098,203 C1
(45) Certificate Issued: Sep. 2, 2014

(54) DISPOSABLE GARMENT AN RELATED MANUFACTURING EQUIPMENT AND METHODS

(75) Inventors: Gregory John Rajala, Neenah, WI (US); Steven Craig Gehling, Oshkosh, WI (US); Paul Daniel Suke, Appleton, WI (US)

(73) Assignee: Kimberly-Clark Worldwide, Inc., Neenah, WI (US)

Reexamination Request:
No. 90/013,127, Jan. 22, 2014

Reexamination Certificate for:
Patent No.: 6,098,203
Issued: Aug. 8, 2000
Appl. No.: 08/959,622
Filed: Oct. 28, 1997

Certificate of Correction issued Jul. 16, 2002

Related U.S. Application Data

(63) Continuation of application No. 08/382,108, filed on Jan. 31, 1995, now Pat. No. 5,745,922.

(51) Int. Cl.
    *A41B 9/00* (2006.01)
(52) U.S. Cl.
    USPC ............. 2/401; 2/111; 2/243.1; 2/403; 2/406; 604/385.29; 604/396

(58) Field of Classification Search
    None
    See application file for complete search history.

(56) References Cited

To view the complete listing of prior art documents cited during the proceeding for Reexamination Control Number 90/013,127, please refer to the USPTO's public Patent Application Information Retrieval (PAIR) system under the Display References tab.

*Primary Examiner* — Patricia Engle

(57) ABSTRACT

This invention pertains to a three dimensional disposable garment, subassemblies of the garment, and apparatus and methods for making the garment and subassemblies. The garment is designed to hold a primary absorbent sanitary pad. The garment may have elasticized leg and waist openings and be stretchable about the hip and stomach regions of a user. The garment provides backup protection to control egress of fluids that leak or seep around or through the primary sanitary pad. The garment includes a secondary absorbent positioned in the crotch area and extending into the body of the disposable garment, front and back, and preferably over the leg elastics to trap, inside the garment, leakage from the primary absorbent, and to prevent strike through onto e.g. outer clothing and bed linen. The apparatus and methods facilitate assembling leg elastics and crotch elastics into the garment subassemblies while assembling a series of garment subassemblies in a continuous web structure at a constant, or relatively constant, continuous and efficient speed.

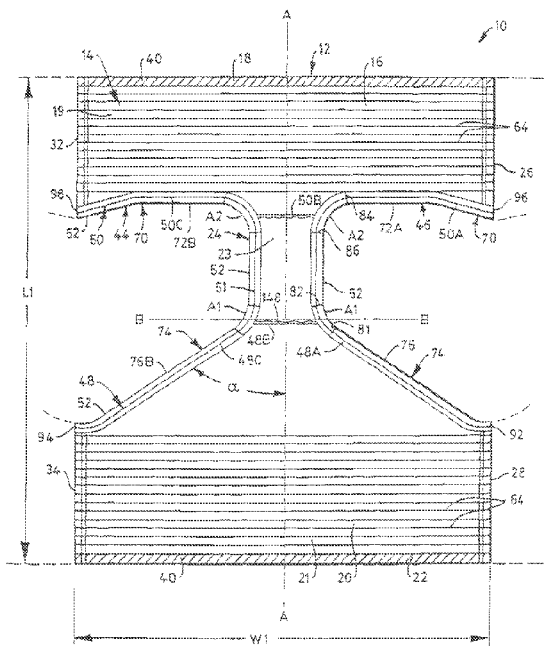
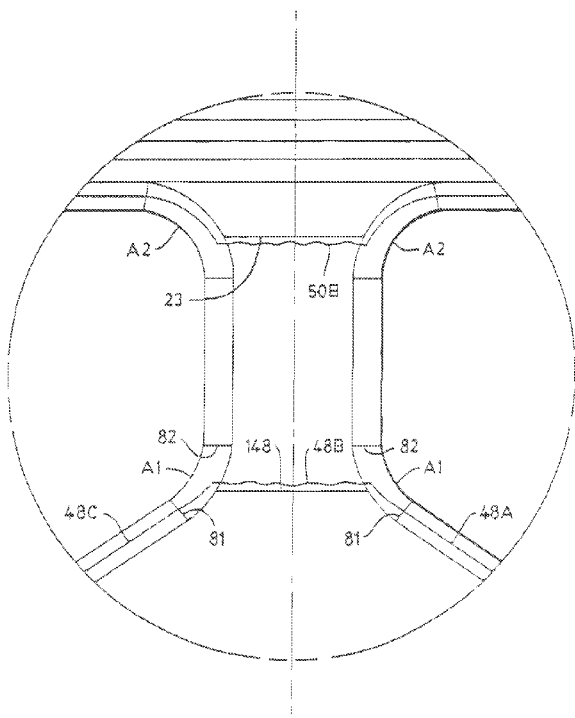

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 9 and 16 is confirmed.

Claims 1-8, 10-15 and 17-24 were not reexamined.

* * * * *

EX PARTE REEXAMINATION CERTIFICATE (10742nd)

United States Patent
Rajala et al.

(10) Number: US 6,098,203 C2
(45) Certificate Issued: Oct. 19, 2015

(54) DISPOSABLE GARMENT AND RELATED MANUFACTURING EQUIPMENT AND METHODS

(75) Inventors: Gregory John Rajala, Neenah, WI (US); Steven Craig Gehling, Oshkosh, WI (US); Paul Daniel Suke, Appleton, WI (US)

(73) Assignee: KIMBERLY-CLARK WORLDWIDE, INC., Neenah, WI (US)

Reexamination Request:
No. 90/012,814, Mar. 22, 2013

Reexamination Certificate for:
Patent No.: 6,098,203
Issued: Aug. 8, 2000
Appl. No.: 08/959,622
Filed: Oct. 28, 1997

Reexamination Certificate C1 6,098,203 issued Sep. 2, 2014

Certificate of Correction issued Jul. 16, 2002

Related U.S. Application Data

(63) Continuation of application No. 08/382,108, filed on Jan. 31, 1995, now Pat. No. 5,745,922.

(51) Int. Cl.
*A41B 9/00* (2006.01)
*A61F 13/15* (2006.01)

(52) U.S. Cl.
CPC ..................................... *A61F 13/15* (2013.01)

(58) Field of Classification Search
USPC ......... 2/401, 406, 111, 243.1; 604/385.2, 396
See application file for complete search history.

(56) References Cited

To view the complete listing of prior art documents cited during the proceeding for Reexamination Control Number 90/012,814, please refer to the USPTO's public Patent Application Information Retrieval (PAIR) system under the Display References tab.

*Primary Examiner* — Matthew C Graham

(57) ABSTRACT

This invention pertains to a three dimensional disposable garment, subassemblies of the garment, and apparatus and methods for making the garment and subassemblies. The garment is designed to hold a primary absorbent sanitary pad. The garment may have elasticized leg and waist openings and be stretchable about the hip and stomach regions of a user. The garment provides backup protection to control egress of fluids that leak or seep around or through the primary sanitary pad. The garment includes a secondary absorbent positioned in the crotch area and extending into the body of the disposable garment, front and back, and preferably over the leg elastics to trap, inside the garment, leakage from the primary absorbent, and to prevent strike through onto e.g. outer clothing and bed linen. The apparatus and methods facilitate assembling leg elastics and crotch elastics into the garment subassemblies while assembling a series of garment subassemblies in a continuous web structure at a constant, or relatively constant, continuous and efficient speed.

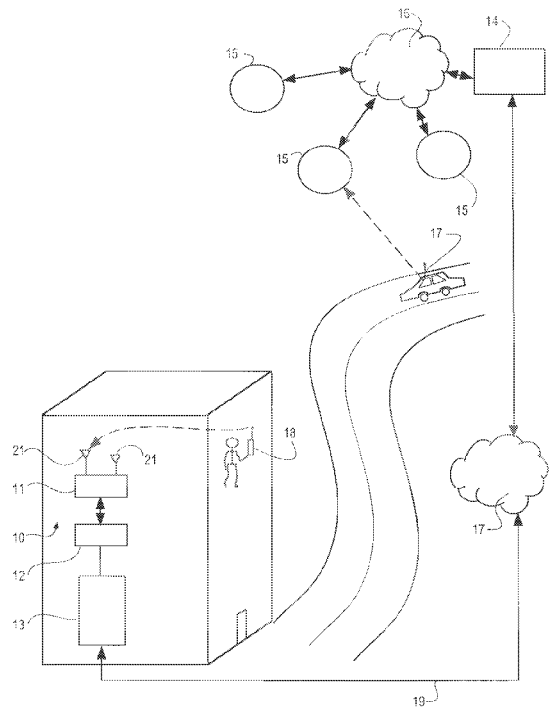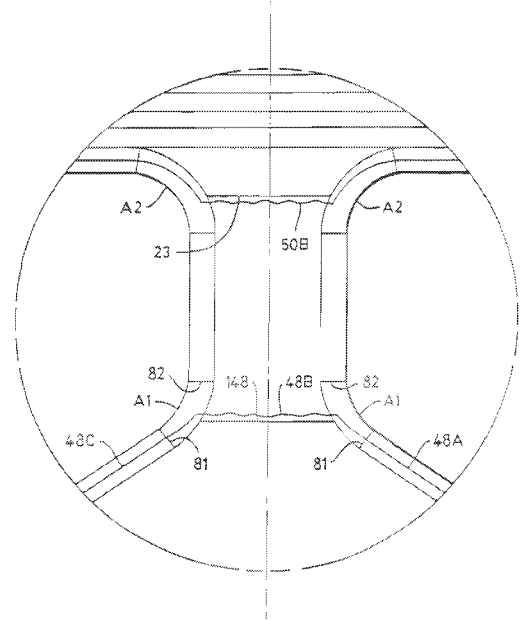

EX PARTE
REEXAMINATION CERTIFICATE

THE PATENT IS HEREBY AMENDED AS INDICATED BELOW.

AS A RESULT OF REEXAMINATION, IT HAS BEEN DETERMINED THAT:

Claim 1 is cancelled.

Claims 2-24 were not reexamined.

\* \* \* \* \*